US011530963B2

(12) United States Patent
Deppermann et al.

(10) Patent No.: US 11,530,963 B2
(45) Date of Patent: *Dec. 20, 2022

(54) AUTOMATED SEED SAMPLER AND METHODS OF SAMPLING, TESTING AND BULKING SEEDS

(71) Applicant: Monsanto Technology LLC, St. Louis, MO (US)

(72) Inventors: Kevin L. Deppermann, St. Charles, MO (US); Michael W. Petersen, Sauk City, WI (US)

(73) Assignee: Monsanto Technology LLC, St. Louis, MO (US)

( * ) Notice: Subject to any disclaimer, the term of this patent is extended or adjusted under 35 U.S.C. 154(b) by 169 days.

This patent is subject to a terminal disclaimer.

(21) Appl. No.: 16/993,178

(22) Filed: Aug. 13, 2020

(65) Prior Publication Data

US 2020/0371002 A1 Nov. 26, 2020

Related U.S. Application Data

(60) Continuation of application No. 16/193,536, filed on Nov. 16, 2018, now Pat. No. 10,775,275, which is a
(Continued)

(51) Int. Cl.
*A01C 1/00* (2006.01)
*G01N 1/04* (2006.01)
(Continued)

(52) U.S. Cl.
CPC ............... *G01N 1/04* (2013.01); *A01C 1/00* (2013.01); *A01C 1/025* (2013.01); *A01H 1/02* (2013.01);
(Continued)

(58) Field of Classification Search
CPC . A01H 4/003; A01H 1/02; A01H 1/04; A01C 1/00; A01C 1/025; G01N 35/04;
(Continued)

(56) References Cited

U.S. PATENT DOCUMENTS 3,850,286 A 11/1974 Tobin, Jr.
3,852,914 A 12/1974 Levengood
(Continued)

FOREIGN PATENT DOCUMENTS

CA 2577890 3/2015
CL 1035-03 5/2003
(Continued)

OTHER PUBLICATIONS

Anklam et al., Analytical methods for detection and determination of genetically modified organisms in agricultural crops and plant-derived food products. (Eur Food Res Technol. 214:3-26), Jan. 2002, 24 pages.
(Continued)

*Primary Examiner* — Trinh T Nguyen
(74) *Attorney, Agent, or Firm* — Harness, Dickey & Pierce, P.L.C.

(57) ABSTRACT

An automated method for sampling seeds generally includes removing material from a seed at an automated sampling station and then, after removing the material from the seed, detecting, by at least one sensor, movement of the seed out of the automated sampling station. The automated method may also include, after removing the material from the seed, transferring the seed from the automated sampling station to a seed container and transferring the material removed from the seed from the automated sampling station to a sample container.

16 Claims, 32 Drawing Sheets

Related U.S. Application Data continuation of application No. 15/268,235, filed on Sep. 16, 2016, now Pat. No. 10,132,725, which is a division of application No. 13/887,738, filed on May 6, 2013, now Pat. No. 9,448,141, which is a continuation of application No. 12/966,715, filed on Dec. 13, 2010, now Pat. No. 8,434,259, which is a continuation of application No. 12/563,895, filed on Sep. 21, 2009, now Pat. No. 7,849,632, which is a continuation of application No. 11/213,432, filed on Aug. 26, 2005, now Pat. No. 7,591,101.

(60) Provisional application No. 60/691,100, filed on Jun. 15, 2005, provisional application No. 60/604,604, filed on Aug. 26, 2004.

(51) Int. Cl.

| | | |
|---|---|---|
| *A01C 1/02* | (2006.01) | |
| *A01H 1/02* | (2006.01) | |
| *A01H 1/04* | (2006.01) | |
| *A01H 4/00* | (2006.01) | |
| *C12Q 1/6895* | (2018.01) | |
| *G01N 35/00* | (2006.01) | |
| *G01N 35/04* | (2006.01) | |

(52) U.S. Cl.
CPC .............. *A01H 1/04* (2013.01); *A01H 4/003* (2013.01); *C12Q 1/6895* (2013.01); *G01N 35/00029* (2013.01); *G01N 35/04* (2013.01); *B07C 2501/009* (2013.01); *C12Q 2600/13* (2013.01); *C12Q 2600/156* (2013.01)

(58) Field of Classification Search
CPC ............ C12Q 2600/156; C12Q 1/6895; C12Q 2600/13; B07C 2501/009
See application file for complete search history.

(56) References Cited

U.S. PATENT DOCUMENTS

| | | | |
|---|---|---|---|
| 4,278,183 | A | 7/1981 | Billington |
| 4,305,130 | A | 12/1981 | Kelley |
| 4,696,308 | A | 9/1987 | Meller et al. |
| 4,827,776 | A | 5/1989 | Gale et al. |
| 5,437,697 | A | 8/1995 | Sebastian et al. |
| 5,677,474 | A | 10/1997 | Rogers |
| 5,746,023 | A | 5/1998 | Hanafey et al. |
| 5,917,927 | A | 6/1999 | Satake et al. |
| 6,307,123 | B1 | 10/2001 | Kriz et al. |
| 6,537,826 | B1 | 3/2003 | Horigane |
| 6,646,264 | B1 | 11/2003 | Modiano et al. |
| 6,809,819 | B1 | 10/2004 | Vinjamoori et al. |
| 6,947,144 | B2 | 9/2005 | Kim et al. |
| 7,044,306 | B2 | 5/2006 | Deppermann |
| 7,067,834 | B2 | 6/2006 | Horigane et al. |
| 7,367,155 | B2 | 5/2008 | Kotyk et al. |
| 7,502,113 | B2 | 3/2009 | Deppermann et al. |
| 7,591,101 | B2 | 9/2009 | Deppermann |
| 7,611,842 | B2 | 11/2009 | Deppermann et al. |
| 7,703,238 | B2 | 4/2010 | Deppermann et al. |
| 7,735,626 | B2 | 6/2010 | Cope et al. |
| 7,767,883 | B2 | 8/2010 | Deppermann et al. |
| 7,830,516 | B2 | 11/2010 | Deppermann et al. |
| 7,832,143 | B2 | 11/2010 | Deppermann et al. |
| 7,849,632 | B2 | 12/2010 | Deppermann et al. |
| 7,877,926 | B2 | 2/2011 | Deppermann et al. |
| 7,915,006 | B2 | 3/2011 | Cope et al. |
| 7,941,969 | B2 | 5/2011 | Deppermann et al. |
| 7,998,669 | B2 | 8/2011 | Deppermann et al. |
| 8,028,469 | B2 | 10/2011 | Deppermann et al. |
| 8,071,845 | B2 | 12/2011 | Deppermann |
| 8,189,901 | B2 | 5/2012 | Modiano et al. |
| 8,245,439 | B2 | 8/2012 | Deppermann et al. |
| 8,312,672 | B2 | 11/2012 | Deppermann et al. |
| 8,434,259 | B2 | 5/2013 | Deppermann |
| 8,436,225 | B2 | 5/2013 | Deppermann et al. |
| 8,443,545 | B2 | 5/2013 | Deppermann et al. |
| 8,501,480 | B2 | 8/2013 | Deppermann et al. |
| 8,539,713 | B2 | 9/2013 | Deppermann et al. |
| 8,561,346 | B2 | 10/2013 | Deppermann et al. |
| 8,959,833 | B2 | 2/2015 | Deppermann et al. |
| 8,997,398 | B2 | 4/2015 | Deppermann et al. |
| 9,003,696 | B2 | 4/2015 | Deppermann et al. |
| 9,027,278 | B2 | 5/2015 | Deppermann et al. |
| 9,383,291 | B2 | 7/2016 | Deppermann et al. |
| 9,448,141 | B2 | 9/2016 | Deppermann |
| 9,551,636 | B2 | 1/2017 | Deppermann et al. |
| 9,986,699 | B2 | 6/2018 | Deppermann et al. |
| 10,132,725 | B2 | 11/2018 | Deppermann |
| 10,254,100 | B2 | 4/2019 | Deppermann et al. |
| 10,542,661 | B2 | 1/2020 | Deppermann et al. |
| 10,705,102 | B2 | 7/2020 | Deppermann et al. |
| 2001/0024796 | A1 | 9/2001 | Selifonov et al. |
| 2002/0070150 | A1 | 6/2002 | Keller et al. |
| 2002/0144458 | A1 | 10/2002 | Hunter et al. |
| 2003/0148258 | A1 | 8/2003 | Kim et al. |
| 2003/0188998 | A1 | 10/2003 | Deppermann |
| 2004/0074822 | A1 | 4/2004 | Horigane et al. |
| 2004/0091888 | A1 | 5/2004 | Nishio et al. |
| 2004/0221335 | A1 | 11/2004 | Shewmaker et al. |
| 2005/0082207 | A1 | 4/2005 | Deppermann |
| 2005/0154221 | A1 | 7/2005 | Lysenko et al. |
| 2006/0046244 | A1 | 2/2006 | Deppermann |
| 2006/0042527 | A1 | 3/2006 | Deppermann |
| 2006/0042528 | A1 | 3/2006 | Deppermann |
| 2007/0048872 | A1 | 3/2007 | Deppermann et al. |
| 2007/0207485 | A1 | 9/2007 | Deppermann et al. |
| 2008/0113367 | A1 | 5/2008 | Becker et al. |
| 2008/0131254 | A1 | 6/2008 | Cope et al. |
| 2008/0131924 | A1 | 6/2008 | Cope et al. |
| 2008/0317279 | A1 | 12/2008 | Deppermann et al. |
| 2009/0025288 | A1 | 1/2009 | Deppermann et al. |
| 2009/0061449 | A1 | 3/2009 | Osborn et al. |
| 2009/0215060 | A1 | 8/2009 | Deppermann et al. |
| 2010/0044356 | A1 | 2/2010 | Cope |
| 2010/0086963 | A1 | 4/2010 | Deppermann et al. |
| 2010/0196950 | A1 | 8/2010 | Deppermann et al. |
| 2010/0263087 | A1 | 10/2010 | Deppermann et al. |
| 2010/0299790 | A1 | 11/2010 | Deppermann |
| 2011/0081716 | A1 | 4/2011 | Deppermann |
| 2011/0129836 | A1 | 6/2011 | Deppermann et al. |
| 2011/0160068 | A1 | 6/2011 | Becker et al. |
| 2011/0217700 | A1 | 9/2011 | Deppermann et al. |
| 2011/0296930 | A1 | 12/2011 | Deppermann et al. |
| 2012/0021411 | A1 | 1/2012 | Deppermann et al. |
| 2012/0079629 | A1 | 3/2012 | Deppermann |
| 2012/0117865 | A1 | 5/2012 | Deppermann |
| 2012/0180386 | A1 | 7/2012 | Deppermann et al. |
| 2012/0288854 | A1 | 11/2012 | Deppermann et al. |
| 2013/0167257 | A1 | 6/2013 | Deppermann et al. |
| 2013/0260366 | A1 | 10/2013 | Deppermann et al. |
| 2014/0020287 | A1 | 1/2014 | Deppermann et al. |
| 2015/0164011 | A1 | 6/2015 | Deppermann |
| 2015/0241322 | A1 | 8/2015 | Deppermann et al. |
| 2015/0355205 | A1 | 12/2015 | Deppermann et al. |
| 2016/0313220 | A1 | 10/2016 | Deppermann et al. |
| 2017/0027102 | A1 | 2/2017 | Fredericksen et al. |
| 2017/0196161 | A1 | 7/2017 | Deppermann et al. |
| 2018/0271042 | A1 | 9/2018 | Butruille et al. |
| 2019/0086297 | A1 | 3/2019 | Deppermann |
| 2019/0234836 | A1 | 8/2019 | Deppermann et al. |
| 2020/0154628 | A1 | 5/2020 | Deppermann et al. |

FOREIGN PATENT DOCUMENTS

| | | |
|---|---|---|
| CL | 673-03 | 2/2004 |
| CL | 2190-05 | 5/2007 |
| CN | 1118235 A | 3/1996 |
| CN | 2510248 | 9/2002 |
| CN | 101052295 | 10/2007 |
| CN | 101080165 | 11/2007 |

(56) References Cited

FOREIGN PATENT DOCUMENTS

| | | |
|---|---|---|
| CN | 101437391 | 5/2009 |
| CN | 101573602 A | 11/2009 |
| CN | 101772300 A | 7/2010 |
| DE | 100 48 643 A1 | 5/2001 |
| DE | 200 22 666 U1 | 1/2002 |
| EP | 0 127 313 | 7/1989 |
| EP | 1 126 268 A1 | 8/2001 |
| EP | 1 401 589 | 1/2003 |
| EP | 1 862 051 A2 | 12/2007 |
| EP | 2 279 658 | 2/2011 |
| GB | 1151988 | 5/1969 |
| GB | 1471076 | 4/1977 |
| JP | 2002 346483 A | 12/2002 |
| RU | 1805835 A3 | 3/1993 |
| RU | 2229210 | 5/2004 |
| SU | 536785 | 11/1976 |
| SU | 1658858 | 6/1991 |
| WO | WO 98/14046 | 4/1998 |
| WO | WO 01/89288 | 11/2001 |
| WO | WO 02/059586 | 8/2002 |
| WO | WO 03/084847 | 10/2003 |
| WO | WO 03/100381 | 12/2003 |
| WO | WO 2004/063333 | 7/2004 |
| WO | WO 2005/031367 | 5/2005 |
| WO | WO 2006/026466 | 3/2006 |
| WO | WO 2006/026467 | 3/2006 |
| WO | WO 2007/025250 | 3/2007 |
| WO | WO 2007/103769 | 9/2007 |
| WO | WO 2008/150798 | 12/2008 |
| WO | WO 2012/012411 | 1/2012 |

OTHER PUBLICATIONS

Arumuganathan, K. & Earle, E.D., *Estimation of Nuclear DNA Content of Plants by Flow Cytometry*, Plant Molecular Biology Reporter 9(3):229-241 (1991).
Benito et al., Rapid identification of Triticeae genotypes from single seeds using the polymerase chain reaction, Plant Molecular Biology 21:181-183, 1993, 3 pages.
Bor-Yaw Lin, Ploidy Barrier to Endosperm Development in Maize (Genetics 107:103-115), May 1984, 13 pages.
Brumback, Jr., et al., "Automating fatty acid analyses from seeds: from field samples to data bases," Lab. Inf. Manage., 21 (1993) pp. 215-222.
Cabrera et al., Open Storage of Soybean Seed in Mississippi, Mississippi Agricultural and Forestry Experiment Station, Sep. 2002. http://msucares.com/pubs/techbulletins/tb204.htm.
Callaway A. S. et al., "High-Throughput Transgene Copy Number Estimation by Competitive PCR", Plant Molecular Biology Reporter, vol. 20, Sep. 2002, pp. 265-277.
Chenault et al., A Non-destructive Seed Sampling Method for PCR-based Analyses in Marker Assisted Selection and Transgene Screening, Peanut Science, 34:38-43 (2007).
Chunwongse J., et al., "Pre-germination genotyping screening using PCR amplification of half-seeds", Theoretical and Applied Genetics, Springer, Berlin, DE, vol. 86, No. 6, Jan. 1993, pp. 694-698.
Churchill, F., *William Johannsen and the Genotype Concept*, Journal of the History of Biology, 7(1):5-30 (1974).
Concibido, V.C. et al., *Introgression of a quantitative trait locus for yield from Glycine soja into commercial sozbean cultivars*, Theor. Appl. Genet. 106:575-582 (2003).
Dahmer et al., "A Rapid Screening Technique for Determining the Lipid Composition of Soybean Seeds", Journal of the American Oil Chemists' Society, Springer, Berlin, DE, vol. 66, Jan. 1989, pp. 543-549.
Demidov Dimitri et al., "Additive effects of the feed-back insensitive bacterial aspartate kinase and the Brazil nut 2S albumin on the methionine content of transgenic narbon bean (*Vicia narbonensis* L.).", Molecular Breeding, vol. 11, No. 3, Apr. 2003, pp. 187-201.
Eder, J. & Chalyk, S., In vivo *haploid induction in maize*, Theor. Appl. Genet. 104:703-708 (2002).

Frisch, M. et al., *Comparison of Selection Strategies for Marker-Assisted Backcrossing of a Gene*, Crop Science 39:1295-1301 (1999).
Gao et al., Development of a seed DNA-based genotyping system for marker-assisted selection in maize, Moi Breeding, 22:477-494 (2008).
Gao et al., Revisiting the Hetero-Fertilization Phenomenon in Maize, PLoS ONE, vol. 6, Issue 1, Jan. 2011, 7 pages.
Gardisser D., On-Farm Drying and Storing, Chapter 15, Dec. 2004, 5 pages http://www.uaex.edu/other_areas/publications/PDF/MP197/chapter15.pdf.
Gillaspie, Jr., Sensitive Method for Testing Peanut Seed Lots for Peanut Stripe and Peanut Mottle Viruses by Immunocapture-Reverse Transcription-Polymerase Chain Reaction, Plant Disease, May 2000, pp. 559-561.
Groos, C. et al., *Study of the relationship between pre-harvest sprouting and grain color by quantitative trait loci analysis in a whitexred grain bread-Wheat cross*, Theor. Appl. Genet. 104:39-47 (2002).
Guidetti Geri, (2007) Viability Myths, <http://waltonfeed.com/self/upack/ag506a1.html>, 4 pages, dated Jun. 21, 2007.
He, L. & Wang, K., *A 384-Well Microtiter-Plate-Based Template Preparation and Sequencing Method*, PCR Cloning Protocols 411-416 (2nd. ed., Humana Press 2002).
Higley P M et al., "Evaluation of Seed Biopsy Methods for Nondestructive Seed Health Testing", Phytopathology, St. Paul, MN, US, vol. 79, No. 10, Jan. 1989, p. 1140.
Horigane et al., *Two-dimensional analysis of kernels using a new sample preparation method*, Chemistry and Biology, 41(6):398-402, Jun. 25, 2003 (Published in Japanese—an English language translation is included).
Horigane, A. et al., *Evaluation of Color Characteristics of Cross-Sectioned Wheat Kernels*, Food Science & Technology Research 9(4):327-331 (2003).
J.P. Hazebroek, "Analysis of genetically modified oils" Progress in Lipid Research 39 (2000) pp. 477-506.
Jones D A L M Barber et al., "An analysis of seed development in *Pisum sativum*L. XVI. Assessing variation for fatty acid content by use of a non-destructive technique for single-seed analysis", Plant Breeding, vol. 114, No. 1, 1995, pp. 81-83.
Jousse et al., Rapid, cost-effective screening of flax genotypes to identify desirable fatty acid compositions, Electronic Journal of Plant Breeding, 1(6):1396-1404 (2010).
Kamiya et al., Rapid DNA Extraction Method from Soybean Seeds, Breeding Science 53:277-279 (2003).
Kang et al., A Rapid DNA Extraction Method for RFLP and PCR Analysis from a Single Dry Seed, Plant Molecular Biology Regorter, 16:1-9 (1998).
Karcz Jagna et al., "Structural and embryological studies of diploid and tetraploid *Arabidopsis thaliana* (L.) Heynah", Acta Biologica Cracoviensia Series Botanica, vol. 42, No. 2, 2000, pp. 113-124.
Kato, A., *Chromosome doubling of haploid maize seedlings using nitrous oxide gas at the flower primordial stage*, Plant Breeding 121:370-377 (2002).
Kisha, T.J. et al., *Genetic Diversity among Soybean Plant Introductions and North American Germglasm*, Crop Science 38:1669-1680 (1998).
Kotyk et al., High-Throughput Determination of Oil Content in Corn Kernels Using Nuclear Magnetic Resonance Imaging, JAOCS, vol. 82, No. 12, 2005, pp. 855-862.
Kramer et al., *Transgenic Avidin Maize is Resistant to Storage Insect Pests*, Nature Biotechnology, vol. 18, Jun. 2000, pp. 670-674.
Krisnangkura K. et al., "Continuous transmethylation of palm oil in an organic solvent", Jaoch, vol. 69, 1992.
Kristensen et al., A Non-Destructive Screening Method for Proanthocyanidin-Free Barley Mutants, Carlsberg Res. Commun., vol. 51, p. 509-513 (1986).
Krysan, Breakthrough Technologies, Ice-Cap. A High-Throughput Method for Capturing Plant Tissue Samples for Genotype Analysis, Plant Physiology, Jul. 2004 vol. 135, pp. 1162-1169.
Li et al., Molecular Mapping Genes Conditioning Reduced Palmitic Acid Content in N87-2122-4 Soybean (Crop Science 42:373-378), 2002, 6 pages.

(56) References Cited

OTHER PUBLICATIONS

Lipman et al., *Tolerance of Liquid-Air Temperature by Seeds of Higher Plants for Sixty Days*, Plant Physiology 392-394 (1934).
Manabe et al., Segregation distortion through female gametophates in interspecific hybrids of tetraploid wheat as revealed by RAPD analysis (Hereditas 131: 47-53), Oct. 1999, 7 pages.
McCarthy, Paul L., et al., "Rapid identification of transformed wheat using a half-seed PCR assay", Biotechnigues, vol. 31, No. 3, Mar. 2002, pp. 560-564.
Meru et al., A non-destructive genotyping system from a single seed for marker-assisted selection in watermelon, GMR Genetics and Molecular Research 12(1):702-709 (2013).
Morrison, *Sampling in Seed Health Testing*, The American Phytopathology, 1999, 89: 1084-1087.
Notice of Opposition to European Patent EP 1869961 (Application No. EP07016960.2) as filed by Syngenta Crop Protection AG on Oct. 25, 2012, 31 pages, Nov. 6, 2012.
Notice of Third Party Observations filed in European Patent EP 1869961 (Application No. EP07016960.2) Dec. 14, 2012, 11 pages.
Preliminary Opinion of Opposition Division relating to Opposition of European Patent EP 1869961 (Application No. EP07016960.2), and related documents including Decision to Maintain (Jul. 28, 2014) and Minutes of the Oral Proceedings before the Opposition Division (Jul. 28, 2014), Dec. 20, 2013, 37 pages.
Notice of Opposition to European Patent EP 2279657 (Application No. EP10184375.3) as filed by Syngenta Crop Protection AG, and related documents including Preliminary Opinion of Opposition Division (Jan. 26, 2015) and Interlocutory Decision of Opposition Division (Jun. 30, 2015), Dec. 11, 2013, 41 pages.
Petition for Inter Partes Review of U.S. Pat. No. 7,832,143, as filed by E.I. du Pont de Nemours and Company (and 24 Exhibits), and related filings including Patent Trial and Appeal Board's Decision Denying Institution of Inter Partes Review, Jan. 8, 2014, 145 pages.
Petition for Inter Partes Review of U.S. Pat. No. 8,028,469, as filed by E.I. du Pont de Nemours and Company (and 25 Exhibits), and related filings including Patent Trial and Appeal Board's Decision Denying Institution of Inter Partes Review, Jan. 8, 2014, 113 pages.
Petition for Inter Partes Review of U.S. Pat. No. 8,071,845, as filed by E.I. du Pont de Nemours and Company (and 25 Exhibits), and related filings including Patent Trial and Appeal Board's Decision Denying Institution of Inter Partes Review, Jan. 8, 2014, 116 pages.
Petition for Inter Partes Review of U.S. Pat. No. 8,245,439, as filed by E.I. du Pont de Nemours and Company (and 27 Exhibits), and related filings including Patent Trial and Appeal Board's Decision Denying Institution of Inter Partes Review, Jan. 8, 2014, 125 pages.
Petition for Inter Partes Review of U.S. Pat. No. 8,312,672, as filed by E.I. du Pont de Nemours and Company (and 34 Exhibits), and related filings including Patent Trial and Appeal Board's Decision Denying Institution of Inter Partes Review, Jan. 8, 2014, 124 pages.
Pioneer Hi-Bred International, Inc., Downloadable Photos—Laser-Assisted Seed Selection, http://www.pioneer.com/web/site/portal/menuiteam.b9e99dcb8e2cfd8ecfe6d10093a0/, printed as of Nov. 25, 2008, 4 pages.
R.K. Downey, Genetic Control of Fatty Acid Biosynthesis in Rapeseed (*Brassica napus* L.) (AOCS 41:475-478), 1964, 4 pages.
R.K.Downey, Methods of Breeding for Oil Quality in Rape (Canadian Journal of Plant Science 43:271-275), Jul. 1963, 7 pages.
Sangtong, V. et al., *Serial Extraction of Endosperm Drillings (SEED)—A Method for Detecting Transgenes and Proteins in Single Viable Maize Kernels*, Plant Molecular Biology Reporter, 19:151-158 (2001).
Schuster Ivan et al., "Correlation between high molecular weight gluten subunits composition and bread-making quality in Brazilian wheat", Brazilian Journal of Genetics, vol. 20, No. 4, Dec. 1997, pp. 667-671.
Sedcole, J.R. "Number of plants necessary to recover a trait," Crop Sci. 17:667 (1977).
Serial Extraction of Endosperm Drillings (SEED)—A Method for Detecting Transgenes and Proteins in Single Viable Maize Kernels, Varaporn Sangton, et al., Plant Molecular Biology Reporter 19: 151-158, Jun. 2001, International Society for Plant Molecular Biology.
Smith et al., *Genetic Purity and Testing Technologies for Seed Quality: A Company Perspective*, Seed Science Research, 1998, vol. 8, pp. 285-293.
Tanksley et al., Seed Banks and Molecular Maps: Unlocking Genetic Potential from the Wild (Science 277:1063-1066) Aug. 1997, 5 pages.
Van Der Mey J A M et al., "Mass Screening for Alkaloid Content in Lupinus-Albus", Applied Plant Science, vol. 1, No. 2, 1987, pp. 80-82.
Varshney et al., Plant Biotechnology and Molecular Markers (Kluwer Academic Publishers; Print ISBN: 1-4020-1911-4; Edited by P.S. Srivastava, Alka Narula, Sheela Srivastava) (Chapter 20), Apr. 2004, 42 pages.
Von Post et al., A High-Throughput DNA Extraction Method for Barley Seed, Euphytica 130: 255-260, 2003.
Wright, H., *Commercial Hybrid Seed Production*, Hybridization of Crop Plants 161-176 (1980).
Zeile, W.L. et al., "A Rapid Non-Destructive Technique for Fatty Acid Determination in Individual Peanut Seed" Peanut Science (1993) 20:9-11 (3 pages).
U.S. Appl. No. 16/193,536, filed Nov. 16, 2018.
U.S. Appl. No. 15/268,235, filed Sep. 16, 2016.
U.S. Appl. No. 13/887,738, filed May 6, 2013.
U.S. Appl. No. 12/966,715, filed Dec. 13, 2010.
U.S. Appl. No. 12/563,895, filed Sep. 21, 2009.
U.S. Appl. No. 11/213,432, filed Aug. 26, 2005.
U.S. Appl. No. 11/213,435: (a) Restriction Requirement dated Jul. 5, 2007; (b) Office Action dated Nov. 15, 2007; (c) Final Office Action dated Apr. 10, 2009; and (d) Notice of Allowance dated Aug. 26, 2009. Both the instant application and U.S. Appl. No. 11/213,435 have priority claims related to U.S. Appl. No. 60/691,100 and U.S. Appl. No. 60/691,100.
U.S. Appl. No. 11/680,611: (a) Restriction Requirement dated Oct. 6, 2008; (b) Office Action dated Apr. 7, 2009; and (c) Notice of Allowance dated Dec. 7, 2009. Both the instant application and U.S. Appl. No. 11/680,611 have priority claims related to U.S. Appl. No. 60/604,604 and U.S. Appl. No. 60/691,100.
U.S. Appl. No. 12/243,739: (a) Restriction Requirement dated May 28, 2009; (b) Office Action dated Nov. 16, 2009; (c) Notice of Allowance dated Jul. 6, 2010; and (d) Notice of Allowance dated Oct. 8, 2010. Both the instant application and U.S. Appl. No. 12/243,739 have priority claims related to U.S. Appl. No. 60/604,604 and U.S. Appl. No. 60/691,100.
U.S. Appl. No. 12/358,985: (a) Notice of Allowance dated Aug. 19, 2010. U.S. Appl. No. 12/358,985 has at least one inventor in common with the current application.
U.S. Appl. No. 12/563,895: (a) Office Action dated Aug. 4, 2010; and (b) Notice of Allowance dated Sep. 21, 2010. Both the instant application and U.S. Appl. No. 12/563,895 have priority claims related to U.S. Appl. No. 60/604,604 and U.S. Appl. No. 60/691,100.
U.S. Appl. No. 12/759,423: (a) Restriction Requirement dated Jun. 15, 2010; and (b) Notice of Allowance dated Sep. 23, 2010. Both the instant application and U.S. Appl. No. 12/759,423 have priority claims related to U.S. Appl. No. 60/604,604 and U.S. Appl. No. 60/691,100.
U.S. Appl. No. 11/510,771: (a) Office Action dated Jan. 6, 2009; (b) Final Office Action dated May 8, 2009; (c) Office Action dated Aug. 6, 2009; (d) Final Office Action dated Apr. 6, 2010; (e) Office Action dated Mar. 14, 2011; (f) Final Office Action dated Sep. 29, 2011; and (g) Notice of Abandonment dated Apr. 18, 2012. U.S. Appl. No. 11/510,771 has inventors in common with the current application.
U.S. Appl. No. 12/767,640: (a) Restriction Requirement, dated Sep. 1, 2010; and (b) Notice of Allowance dated Jan. 10, 2011. Both the instant application and U.S. Appl. No. 12/767,640 have priority claims related to U.S. Appl. No. 60/604,604 and U.S. Appl. No. 60/691,100.
U.S. Appl. No. 12/848,751: (a) Restriction Requirement dated Oct. 13, 2010; (b) Office Action dated Feb. 11, 2011; and (c) Notice of Allowance dated Aug. 30, 2011. Both the instant application and

(56) References Cited

OTHER PUBLICATIONS

U.S. Appl. No. 12/848,751 have priority claims related to U.S. Appl. No. 60/604,604 and U.S. Appl. No. 60/691,100.
U.S. Appl. No. 11/680,180: (a) Restriction Requirement dated Jan. 6, 2010; (b) Office Action dated Jun. 8, 2010; (c) Final Office Action dated Dec. 8, 2010; and (d) Notice of Allowance dated Jun. 24, 2011. U.S. Appl. No. 11/680,180 has inventors in common with the current application.
U.S. Appl. No. 12/128,279: (a) Office Action dated Aug. 9, 2010; (b) Notice of Allowance dated Jan. 6, 2011; and (c) Notice of Allowance dated May 26, 2011. U.S. Appl. No. 12/128,279 has at least one inventor in common with the current application.
U.S. Appl. No. 13/251,993: (a) Office Action dated Dec. 22, 2011; and (b) Notice of Allowance dated Apr. 13, 2012. U.S. Appl. No. 13/251,993 has at least one inventor in common with the current application.
U.S. Appl. No. 13/210,212: (a) Office Action dated Dec. 23, 2011; and (b) Notice of Allowance dated May 24, 2013. U.S. Appl. No. 13/210,212 has inventors in common with the current application.
U.S. Appl. No. 13/108,762: (a) Office Action dated Aug. 4, 2011; and (b) Notice of Allowance dated Jul. 20, 2012. U.S. Appl. No. 13/108,762 has at least one inventor in common with the current application.
U.S. Appl. No. 13/016,242: (a) Office Action dated May 4, 2011; (b) Office Action dated Oct. 27, 2011; (c) Office Action dated Feb. 24, 2012; (d) Final Office Action dated Jul. 3, 2012; (e) Notice of Allowance dated Oct. 29, 2012; and (f) Notice of Allowance dated Jul. 1, 2013. Both the instant application and U.S. Appl. No. 13/016,242 have priority claims related to U.S. Appl. No. 60/604,604 and U.S. Appl. No. 60/691,100.
U.S. Appl. No. 12/966,715: (a) Office Action dated Feb. 17, 2012; (b) Notice of Allowance dated Aug. 21, 2012; (c) Notice of Allowance dated Jan. 9, 2013; and (d) Notice of Allowance dated Jan. 24, 2013. Both the instant application and U.S. Appl. No. 12/966,715 have priority claims related to U.S. Appl. No. 60/604,604 and U.S. Appl. No. 60/691,100.
U.S. Appl. No. 13/407,348: (a) Office Action dated Jul. 16, 2012; and (b) Notice of Allowance dated Apr. 1, 2013. U.S. Appl. No. 13/407,348 has inventors in common with the current application.
U.S. Appl. No. 13/556,742: (a) Office Action dated Oct. 11, 2012; and (b) Notice of Allowance dated Feb. 1, 2013. U.S. Appl. No. 13/556,742 has inventors in common with the current application.
U.S. Appl. No. 13/302,657: (a) Office Action dated Feb. 10, 2012; (b) Notice of Allowance dated Jul. 24, 2012; and (c) Notice of Allowance dated Jan. 17, 2013. Both the instant application and U.S. Appl. No. 13/302,657 have priority claims related to U.S. Appl. No. 60/604,604 and U.S. Appl. No. 60/691,100.
U.S. Appl. No. 13/897,024: (a) Office Action dated Dec. 13, 2013; (b) Restriction Requirement dated Sep. 16, 2014; and (c) Notice of Allowance dated Dec. 3, 2014. U.S. Appl. No. 13/897,024 has inventors in common with the current application.
U.S. Appl. No. 14/635,738: (a) Office Action dated Feb. 26, 2016; and (b) Notice of Allowance dated Sep. 15, 2016. U.S. Appl. No. 14/635,738 has inventors in common with the current application.
U.S. Appl. No. 14/032,850: (a) Office Action dated Dec. 10, 2013; and (b) Notice of Allowance dated Jan. 14, 2015. U.S. Appl. No. 14/032,850 has inventors in common with the current application.
U.S. Appl. No. 14/685,033: (a) Notice of Allowance dated Mar. 3, 2016. U.S. Appl. No. 14/685,033 has inventors in common with the current application.
U.S. Appl. No. 13/887,738: (a) Restriction Requirement dated Mar. 11, 2015; (b) Office Action dated Sep. 4, 2015; and (c) Notice of Allowance dated May 18, 2016. Both the instant application and U.S. Appl. No. 13/887,738 have priority claims related to U.S. Appl. No. 60/604,604 and U.S. Appl. No. 60/691,100.
U.S. Appl. No. 13/680,603: (a) Office Action dated Sep. 10, 2013; and (b) Notice of Allowance dated Jul. 1, 2014. Both the instant application and U.S. Appl. No. 13/680,603 have priority claims related to U.S. Appl. No. 60/604,604 and U.S. Appl. No. 60/691,100.
U.S. Appl. No. 14/629,235: (a) Restriction Requirement dated Jul. 11, 2017; and (b) Notice of Allowance dated Feb. 8, 2018. Both the instant application and U.S. Appl. No. 14/629,235 have priority claims related to U.S. Appl. No. 60/604,604 and U.S. Appl. No. 60/691,100.
U.S. Appl. No. 13/186,126: (a) Office Action dated May 23, 2014; and (b) Notice of Allowance dated Dec. 5, 2014. U.S. Appl. No. 13/186,126 has inventors in common with the current application.
U.S. Appl. No. 14/685,047: (a) Restriction Requirement dated May 18, 2017; (b) Office Action dated Sep. 15, 2017; (c) Final Office Action dated Jul. 6, 2018; (d) Office Action dated Sep. 20, 2019; and (e) Notice of Allowance dated Mar. 5, 2020. U.S. Appl. No. 14/685,047 has inventors in common with the current application.
U.S. Appl. No. 15/200,411: (a) Restriction Requirement dated Dec. 1, 2017; (b) Office Action dated Jun. 11, 2018; and (c) Notice of Allowance dated Nov. 28, 2018. U.S. Appl. No. 15/200,411 has inventors in common with the current application.
U.S. Appl. No. 15/268,235: (a) Office Action dated Nov. 15, 2017 and (b) Notice of Allowance dated Jul. 18, 2018. Both the instant application and U.S. Appl. No. 15/268,235 have priority claims related to U.S. Appl. No. 60/604,604 and U.S. Appl. No. 60/691,100.
U.S. Appl. No. 15/411,531: (a) Restriction Requirement dated Jun. 26, 2018; (b) Office Action dated Oct. 29, 2018, (c) Final Office Action dated May 9, 2019; and (d) Notice of Allowance dated Sep. 11, 2019. U.S. Appl. No. 15/411,531 has inventors in common with the current application.
U.S. Appl. No. 15/996,080: (a) Restriction Requirement dated Dec. 23, 2019; and (b) Office Action dated Jun. 23, 2020. Both the instant application and U.S. Appl. No. 15/996,080 have priority claims related to U.S. Appl. No. 60/604,604 and U.S. Appl. No. 60/691,100.
U.S. Appl. No. 16/193,536: (a) Office Action dated Mar. 7, 2019; (b) Restriction Requirement dated Oct. 22, 2019; and (c) Notice of Allowance dated May 12, 2020. Both the instant application and U.S. Appl. No. 16/193,536 have priority claims related to U.S. Appl. No. 60/604,604 and U.S. Appl. No. 60/691,100.
CL 2189-05: (a) Office Action; (b) Office Action; (c) Office Action; and (d) Grant of Application dated Oct. 28, 2011. These Actions were not in English. Applicant provided English language comments regarding the Actions for convenience to the Examiner. Both the instant application and Chilean Application No. 2189-05 have priority claims related to U.S. Appl. No. 60/604,604 and U.S. Appl. No. 60/691,100.
CN 200580036539.1: (a) Office Action dated Jun. 19, 2009; (b) Office Action dated Sep. 30, 2011; and (c) Intent to Grant dated Apr. 9, 2012. These Actions were not in English. Applicant provided English language comments regarding the Actions for convenience to the Examiner. Chinese Application Serial No. 200580036539.1 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
RU 2007110842: (a) Office Action dated Dec. 1, 2009; (b) Office Action dated Mar. 30, 2010; and (c) Decision to Grant dated Jun. 22, 2010. These Actions were not in English. Applicant provided English language comments regarding the Actions for convenience to the Examiner. Russian Patent Application Serial No. 2007110842 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
UA 200702962: (a) Office Action dated Feb. 4, 2010; (b) Decision to Grant dated Apr. 19, 2010. These Actions were not in English. Applicant provided English language comments regarding the Actions for convenience to the Examiner. Ukrainian Patent Application Serial No. 200702962 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
MX/A/2007/002306: (a) Office Action dated Feb. 11, 2010; and (b) Notice of Allowance dated Aug. 30, 2010. These Actions were not in English. Applicant provided English language comments regarding the Actions for convenience to the Examiner. Mexican Patent

(56) References Cited

OTHER PUBLICATIONS

Application Serial No. MX/A/2007/002306 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
IN 1444/DELNP/2007: (a) Office Action dated Feb. 19, 2010; (b) Notice of Hearing dated Mar. 14, 2011; and (c) Grant of Patent dated Nov. 8, 2011. Indian Patent Application Serial No. 1444/DELNP/2007 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
EP 05792743.6: (a) Extended European Search Report dated Jul. 18, 2011; (b) Publication of Extended European Search Report dated Aug. 4, 2011; (c) Official Communication dated Jun. 22, 2012; and (d) Intention to Grant dated May 27, 2013. European Patent Application Serial No. 05792743.6 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
EP 10184375.3: (a) Extended European Search Report dated Jul. 18, 2011; (b) Publication of Extended Search Report dated Aug. 22, 2011; (c) Intention to Grant dated Sep. 6, 2012; and (d) Decision to Grant dated Feb. 7, 2013. European Patent Application Serial No. 10184375.3 is a divisional application of EP 05792743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100. Additional filings relating to the Notice of Opposition to European Patent EP 2279657 (Application No. EP07016960.2) (see item #184 in the Form 1449 filed herewith), including (a) Notice of Appeal dated Sep. 23, 2015; (b) Opponent's Grounds of Appeal dated Nov. 23, 2015; (c) Minutes of the Oral Proceedings dated Feb. 27, 2019; and (d) Decision of Technical Board of Appeal dated Mar. 11, 2019. European Patent Application Serial No. 10184375.3 is a divisional application of EP 05792743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
EP 10185374.5: (a) Extended European Search Report dated Jul. 18, 2011; (b) Publication of Extended Search Report dated Aug. 22, 2011; (c) Official Communication dated Nov. 9, 2012; (d) Intention to Grant dated Jan. 20, 2014; (e) Intention to Grant dated Sep. 29, 2014; and (f) Decision to Grant dated Feb. 19, 2015. European Patent Application Serial No. 10185374.5 is a divisional application of EP 05792743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
EP 07016960.2: (a) Partial European Search Report dated Dec. 29, 2008; (b) Extended European Search Report, dated Mar. 19, 2009; (c) Office Communication, dated Oct. 21, 2009; (d) Office Communication dated Jul. 15, 2010; (e) Intention to Grant, dated Aug. 26, 2011; and (f) Decision to Grant dated Dec. 30, 2011. European Patent Application Serial No. 07 016 960.2 is a divisional application of EP 05792743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100. Additional filings relating to the Notice of Opposition to European Patent EP 1869961 (Application No. EP07016960.2) (see item #181 in the Form 1449 filed herewith), including (a) Notice of Appeal dated Oct. 7, 2014; (b) Grounds of Appeal dated Dec. 5, 2014; (c) Opponent's Grounds of Appeal dated Dec. 8, 2014; (d) Board of Appeal Communication dated Feb. 6, 2018; and (e) Decision of Technical Board of Appeal dated May 4, 2018. European Patent Application Serial No. 07 016 960.2 is a divisional application of EP 05792743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
EP 07016961.0: (a) Partial European Search Report dated Jan. 30, 2008; (b) Extended European Search Report dated Apr. 18, 2008; (c) Office Communication dated Mar. 21, 2017; (d) Intent to Grant dated Nov. 22, 2017; and (e) Decision to Grant dated Apr. 6, 2018. European Patent Application Serial No. 07 016 961.0 is a divisional application of EP 05 792 743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
EP 07016962.8: (a) Extended European Search Report dated Jan. 5, 2009; (b) Office Communication dated Oct. 22, 2009; (c) Office Communication dated Jul. 15, 2010; and (d) Notice of Loss of Rights dated Mar. 3, 2011. European Patent Application Serial No. 07 016 962.8 is a divisional application of EP 05 792 743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
AR P050103585: (a) Office Action; and (b) Grant of Patent, dated Feb. 29, 2012. Both the instant application and Argentina Application Serial No. P050103585 have priority claims related to U.S. Appl. No. 60/604,604 and U.S. Appl. No. 60/691,100.
CA 2,577,890: (a) Official Action dated Jul. 4, 2012; (b) Official Action dated Oct. 10, 2013; and (c) Notice of Allowance dated Jul. 11, 2014. Canadian Patent Application No. 2,577,890 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
ID W00200703621: (a) Official Action dated Sep. 17, 2014. The Official Action is not in the English language. Applicant provides an English language translation for convenience to the Examiner. Indonesian Patent Application No. W00200703621 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
CN 201210217124.6: (a) Office Action dated Apr. 8, 2013 and (b) Notification of Grant dated Feb. 10, 2014. The Office Actions are not in the English language. Applicant provided English language comments regarding the Actions for convenience to the Examiner. Chinese Application No. 201210217124.6 is a divisional of Chinese Application No. 200580036539.1, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
CN 201210217218.3: (a) Office Action dated Jun. 21, 2013; (b) Office Action dated Apr. 25, 2014; (c) Office Action dated Dec. 29, 2014; and (d) Notification of Grant dated Sep. 8, 2015. The Office Actions are not in the English language. Applicant provides English language comments regarding the Actions for convenience to the Examiner. Chinese Application No. 201210217218.3 is a divisional of Chinese Application No. 200580036539.1, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.
AR P120100439: (a) Office Action dated Dec. 22, 2016; (b) Office Action dated Feb. 26, 2018; and (c) Office Action dated Jan. 16, 2019. The Office Actions are not in the English language. Applicant provides English language comments regarding the Actions for convenience to the Examiner. Both the instant application and Argentina Application Serial No. P120100439 have priority claims related to U.S. Appl. No. 60/604,604 and U.S. Appl. No. 60/691,100.

(56) References Cited

OTHER PUBLICATIONS

EP 14166434.2: (a) Office Action dated Oct. 17, 2014; (b) Extended Search Report dated Feb. 28, 2015; (c) Office Action dated Nov. 9, 2016; (d) Office Action dated Sep. 19, 2017; (e) Summons to Attend Oral Proceeding dated Nov. 9, 2018; and (f) Intent to Grant dated Oct. 15, 2019. European Patent Application Serial No. 14166434.2 is a divisional application of EP 05 792 743.6, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

IN 3763/DELNP/2011: (a) Office Action dated Sep. 7, 2017; and (b) Grant of Application dated Aug. 13, 2019. Indian Patent Application IN 3763/DELNP/2011 is a divisional of Indian Patent Application Serial No. 1444/DELNP/2007, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

IN 3764/DELNP/2011: (a) Office Action dated May 15, 2017; (b) Notice of Hearing dated Mar. 5, 2018; and (c) Grant of Application dated Jun. 8, 2018. Indian Patent Application IN 3764/DELNP/2011 is a divisional of Indian Patent Application Serial No. 1444/DELNP/2007, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

IN 3765/DELNP/2011: (a) Office Action dated Jul. 11, 2017; and (b) Grant of Application dated Apr. 25, 2018. Indian Patent Application IN 3765/DELNP/2011 is a divisional of Indian Patent Application Serial No. 1444/DELNP/2007, which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

BR PI0514685-2: (a) Office Action dated May 28, 2015; (b) Office Action dated Oct. 9, 2015; (c) Office Action dated Oct. 11, 2018; (d) Notice of Allowance dated Jan. 23, 2019; and (e) Notification of Grant dated Apr. 29, 2019. The Office Actions are not in the English language. Applicant provided English language comments regarding the Actions for convenience to the Examiner. Brazilian Patent Application No. PI0514685-2 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

BR 122015017827-4: (a) Office Action dated Apr. 12, 2016; (b) Office Action dated Oct. 27, 2016; (c) Office Action dated Mar. 22, 2017; and (d) Notice of Allowance dated Dec. 11, 2019. The Office Actions are not in the English language. Applicant provided English language comments regarding the Actions for convenience to the Examiner. Brazilian Patent Application No. BR 122015017827-4 is a divisional of Brazilian Patent Application No. PI0514685-2 which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

TH 0501004001: (a) Office Action dated Dec. 21, 2018; and (b) Grant of Application dated Oct. 10, 2019. Thailand Patent Application No. 0501004001 is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

TH 1901000613: (a) Office Action dated Jul. 3, 2020. The Office Action is not in the English language. Applicant provides an English language summary for convenience to the Examiner. Thailand Patent Application No. 1901000613 is a divisional of Thailand Application No. 0501004001 which is a national phase patent application of international PCT patent application No. PCT/US2005/030478. Both the instant application and PCT/US2005/030478 have priority claims related to U.S. Appl. No. 60/604,604 and U.S. Appl. No. 60/691,100.

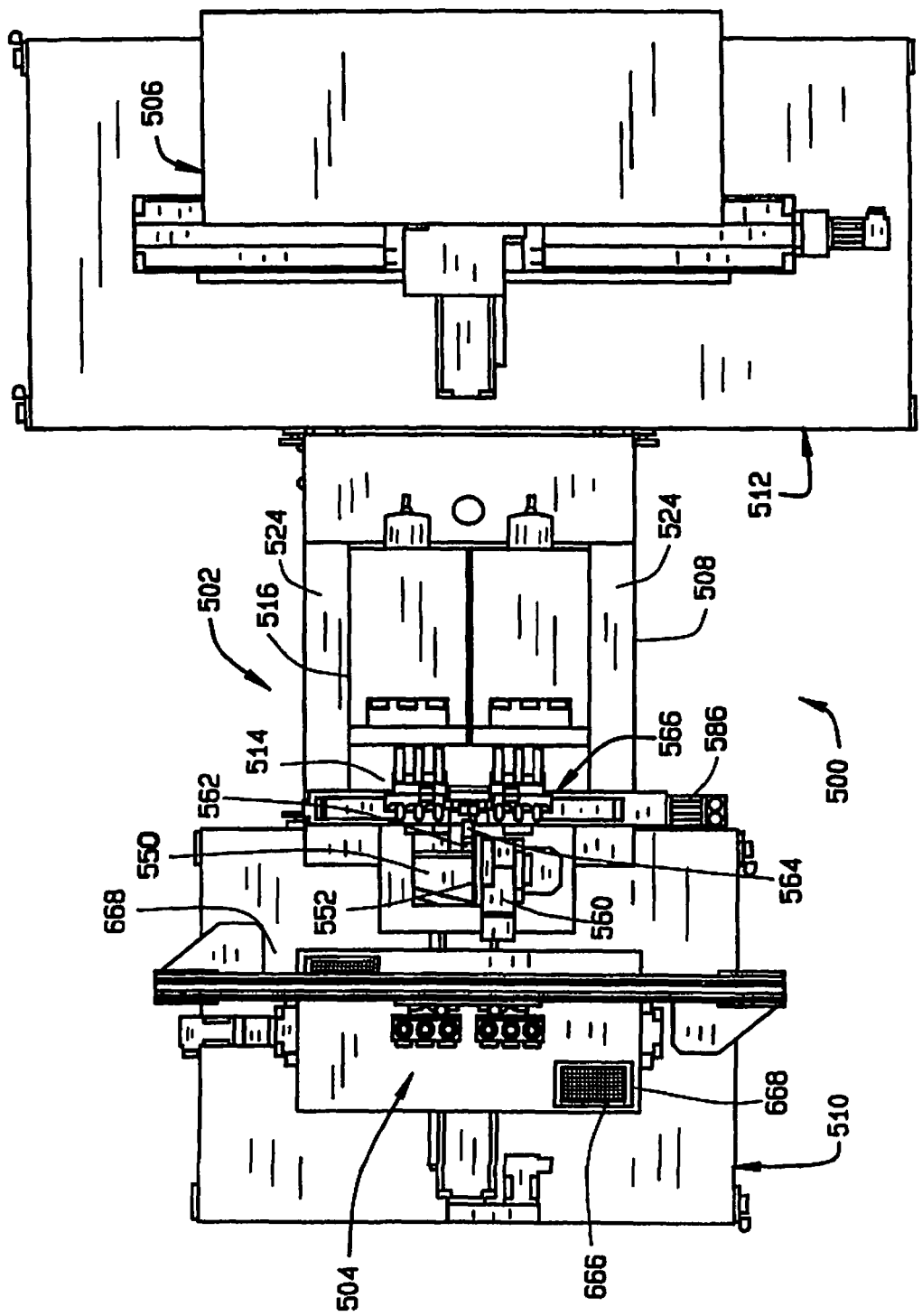

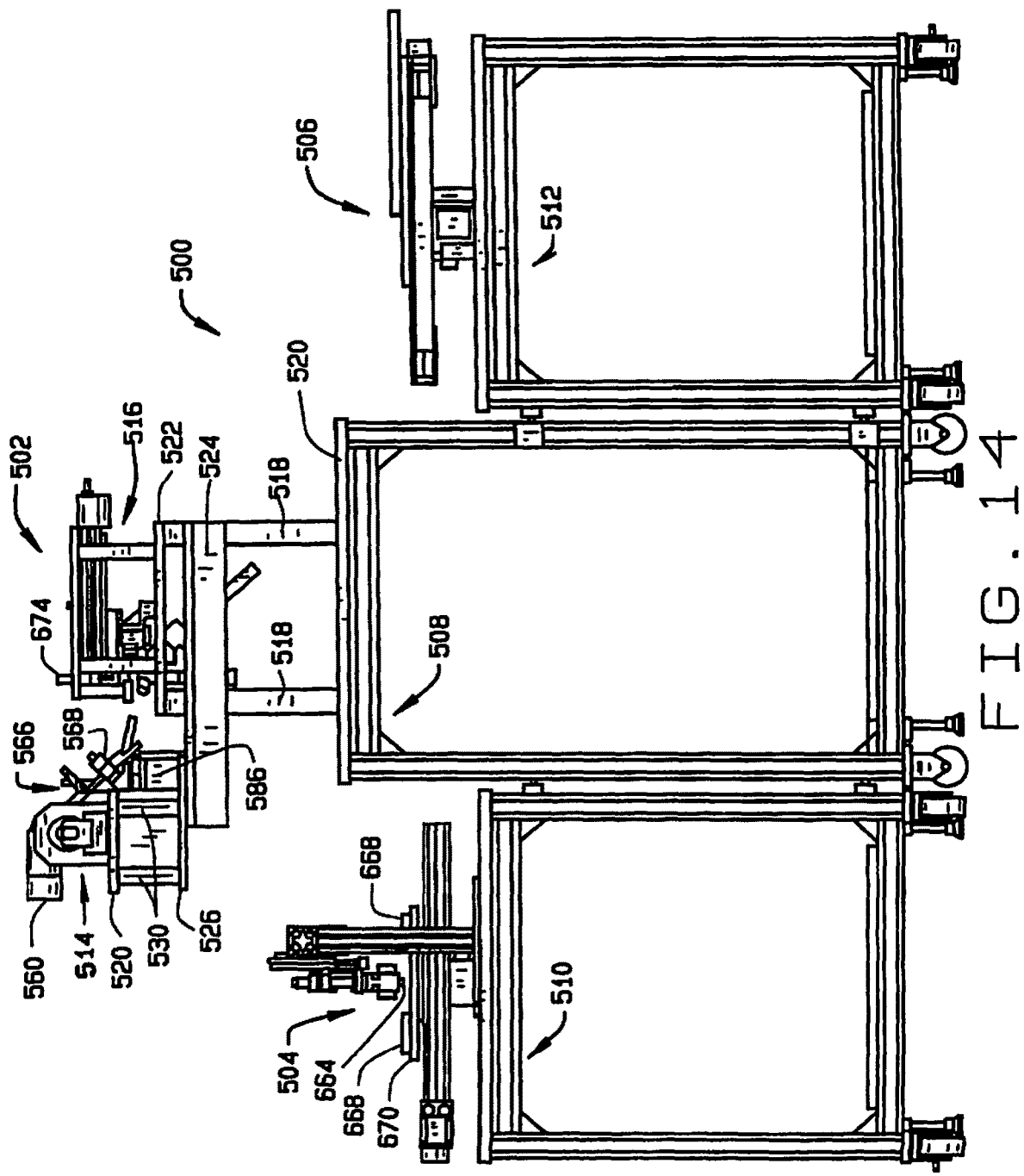

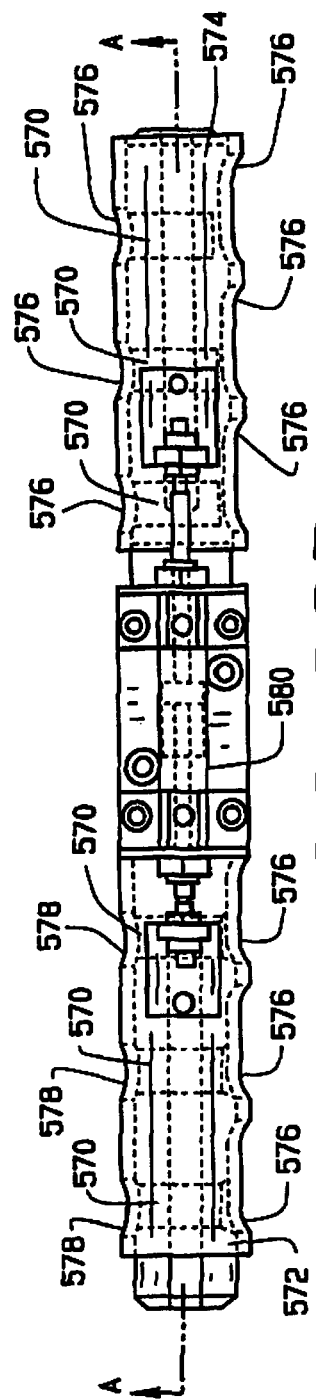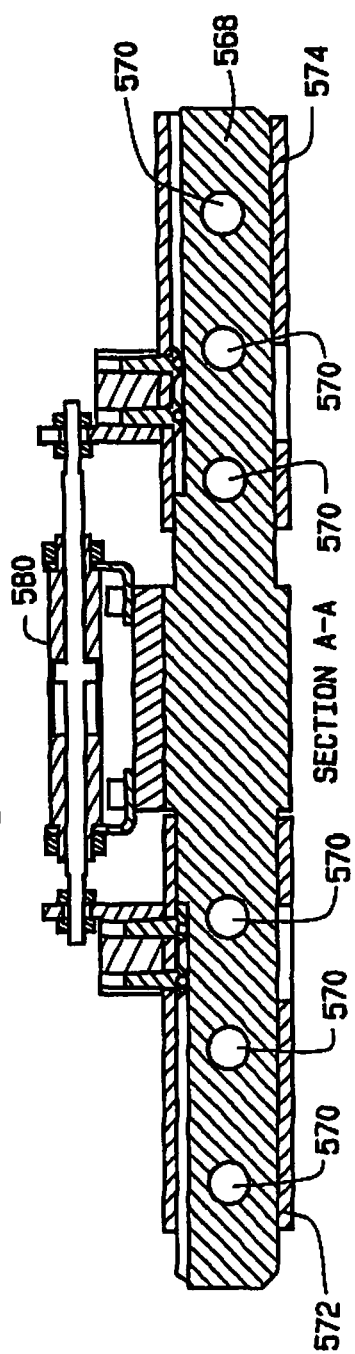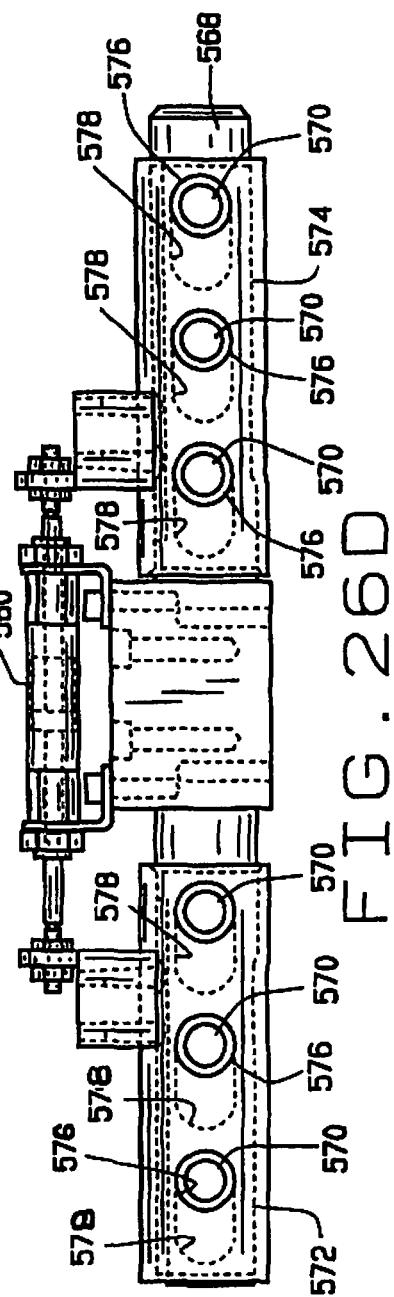

AUTOMATED SEED SAMPLER AND METHODS OF SAMPLING, TESTING AND BULKING SEEDS

CROSS-REFERENCE TO RELATED APPLICATIONS

This application is a continuation of U.S. patent application Ser. No. 16/193,536 filed Nov. 16, 2018, which is a continuation of U.S. patent application Ser. No. 15/268,235 filed Sep. 16, 2016 (now U.S. Pat. No. 10,132,725), which is a divisional of U.S. patent application Ser. No. 13/887,738, filed May 6, 2013 (now U.S. Pat. No. 9,448,141), which is a continuation of U.S. patent application Ser. No. 12/966,715, filed Dec. 13, 2010 (now U.S. Pat. No. 8,434,259), which is a continuation of U.S. patent application Ser. No. 12/563,895, filed Sep. 21, 2009 (now U.S. Pat. No. 7,849,632), which is a continuation of U.S. patent application Ser. No. 11/213,432, filed Aug. 26, 2005 (now U.S. Pat. No. 7,591,101), which claims priority to U.S. Provisional Application Ser. No. 60/604,604, filed Aug. 26, 2004, and U.S. Provisional Application Ser. No. 60/691,100, filed Jun. 15, 2005. The entire disclosure of each of these applications is incorporated herein by reference.

BACKGROUND

This disclosure relates to systems and methods for taking samples from biological materials such as seeds.

In plant development and improvement, genetic improvements are made in the plant, either through selective breeding or genetic manipulation, and when a desirable improvement is achieved, a commercial quantity is developed by planting and harvesting seeds over several generations. Not all seeds express the desired traits, and thus these seeds need to be culled from the population. To speed up the process of bulking up the population, statistical samples are taken and tested to cull seeds from the population that do not adequately express the desired trait. However this statistical sampling necessarily allows some seeds without the desirable trait to remain in the population, and also can inadvertently exclude some seeds with the desirable trait from the desired population.

SUMMARY

The present disclosure generally relates to systems and methods of non-destructively sampling material from seeds. The methods are particularly adapted for automation, which permits greater sampling than was previously practical. With automated, non-destructive sampling permitted by at least some of the embodiments of this disclosure, it is possible to test every seed in the population, and cull those seeds that do not express the desired trait. This greatly speeds up the process of bulking a given seed population, and can result in an improved final population.

Example embodiments of this disclosure facilitate the testing of most or all of the seeds in a population before planting, so that time and resources are not wasted in growing plants without the desired traits.

In one example embodiment, a seed sampler system generally includes an automated sampling station configured to orient a seed and remove a tissue sample from the oriented seed.

In one example embodiment, a seed sampler system generally includes a support configured to orient a seed received by the support, and an automated sampling mechanism configured to remove a tissue sample from the oriented seed.

Example embodiments of the present disclosure may facilitate the automated, non-destructive sampling of seeds. They may permit the testing and sorting of large volumes of seeds, thereby facilitating the bulking up of seed populations with desirable traits. These and other features and advantages will be in part apparent, and in part pointed out hereinafter.

BRIEF DESCRIPTION OF THE DRAWINGS

FIG. 13 is a top plan view of a high throughput seed sampler system in accordance with the principles of this disclosure;

FIG. 14 is a side elevation view of the high throughput seed sampler system;

FIG. 26B is a side elevation view of the feeding mechanism;

FIG. 26C is a longitudinal cross-sectional view of the feeding mechanism, taken along the plane of line 26C-26C in FIG. 26B;

FIG. 26D is a bottom plan view of the feeding mechanism;

Corresponding reference numerals indicate corresponding parts throughout the several views of the drawings.

DETAILED DESCRIPTION

Figure 1:
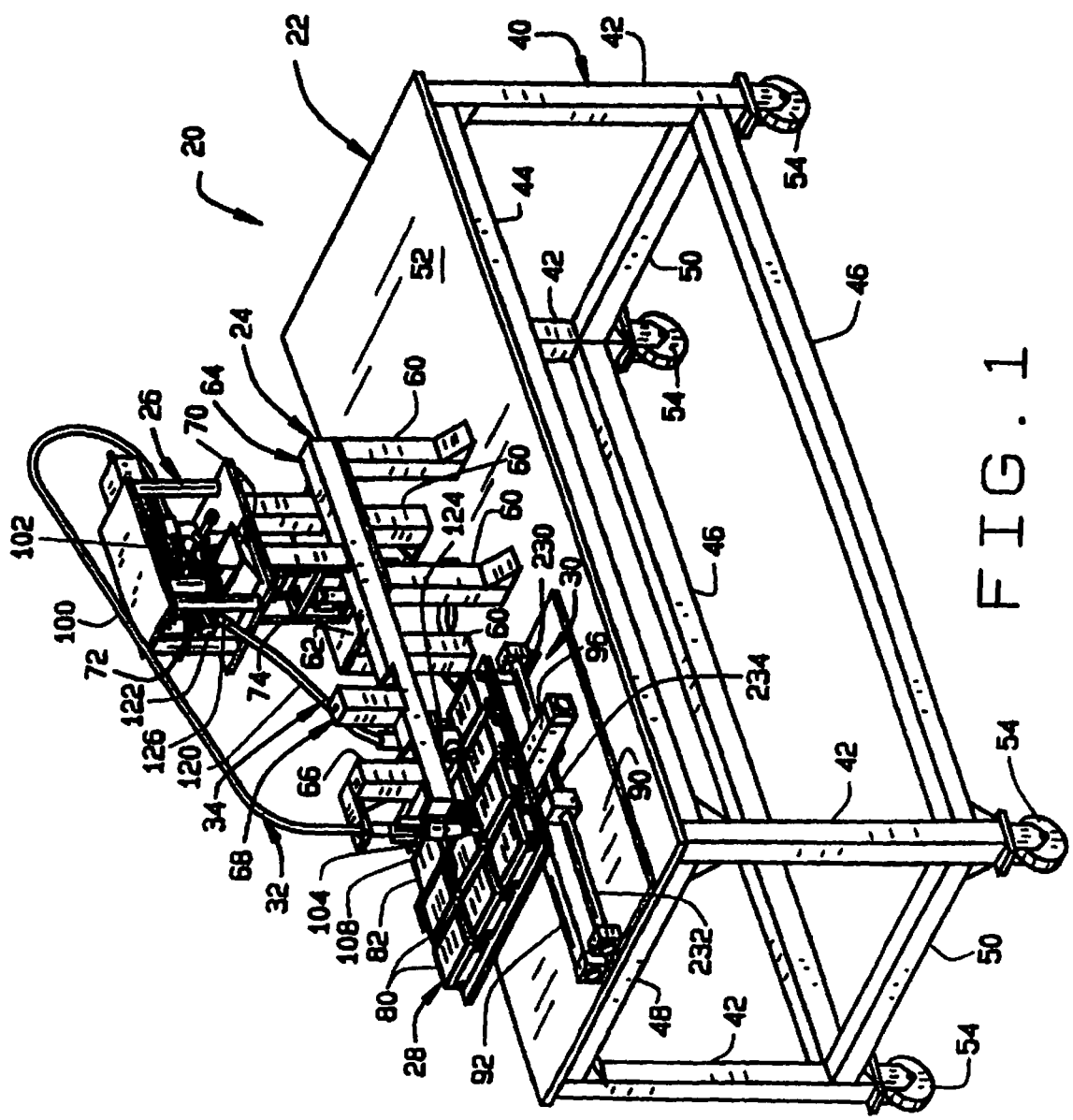
FIG. 1 is a perspective view of a first embodiment of a seed sampler system constructed according to the principles of this disclosure.

A first embodiment of an automated seed sampler system constructed according to the principles of the present disclosure is indicated generally as 20 in FIG. 1. The seed sampler system 20 is adapted to isolate a seed from a hopper, feed it to a sampling station, scrape a sample from the seed, convey the sample to a sample container, and convey the seed to a corresponding seed container. As shown in FIG. 1, the seed sampler system comprises a support 22, a frame 24 on the support; a sampler assembly 26, a stage 28 mounted on a two-dimensional translation mechanism 30, a seed conveyor 32 for transporting seeds from the seed sampler assembly, and a sample conveyor 34 for transporting a sample removed from a seed to the seed sampler assembly.

As shown in FIG. 1, in the first preferred embodiment the support 22 comprises a wheeled cart 40, having a four of vertical posts 42 connected by upper and lower longitudinal members 44 and 46, at the front and back, and upper and lower transverse members 48 and 50 at the left and right sides, and a table top 52 mounted thereon. A caster 54 can be mounted at the bottom of each post 42 to facilitate moving the support 22. The details of the construction of the support 22 are not critical to the disclosure, and thus the support 22 could have some other configuration without departing from the principles of this disclosure As also shown in FIG. 1, the frame 24 comprises four vertically extending stanchions 60 mounted on the table top 52, which support a generally horizontal plate 62. The sampler assembly 26 is mounted on the plate 62, as described in more detail below. An arbor 64 is also mounted on the plate, and extends generally horizontally therefrom. The free end of the arbor 64 has first and second vertical posts 66 and 68 for mounting a seed conveyor 32 and parts of the sample conveyor 34, respectively. The details of the construction of the frame 24 are not critical to the disclosure, and thus the frame could have some other configuration without departing from the principles of this disclosure.

Figure 2:
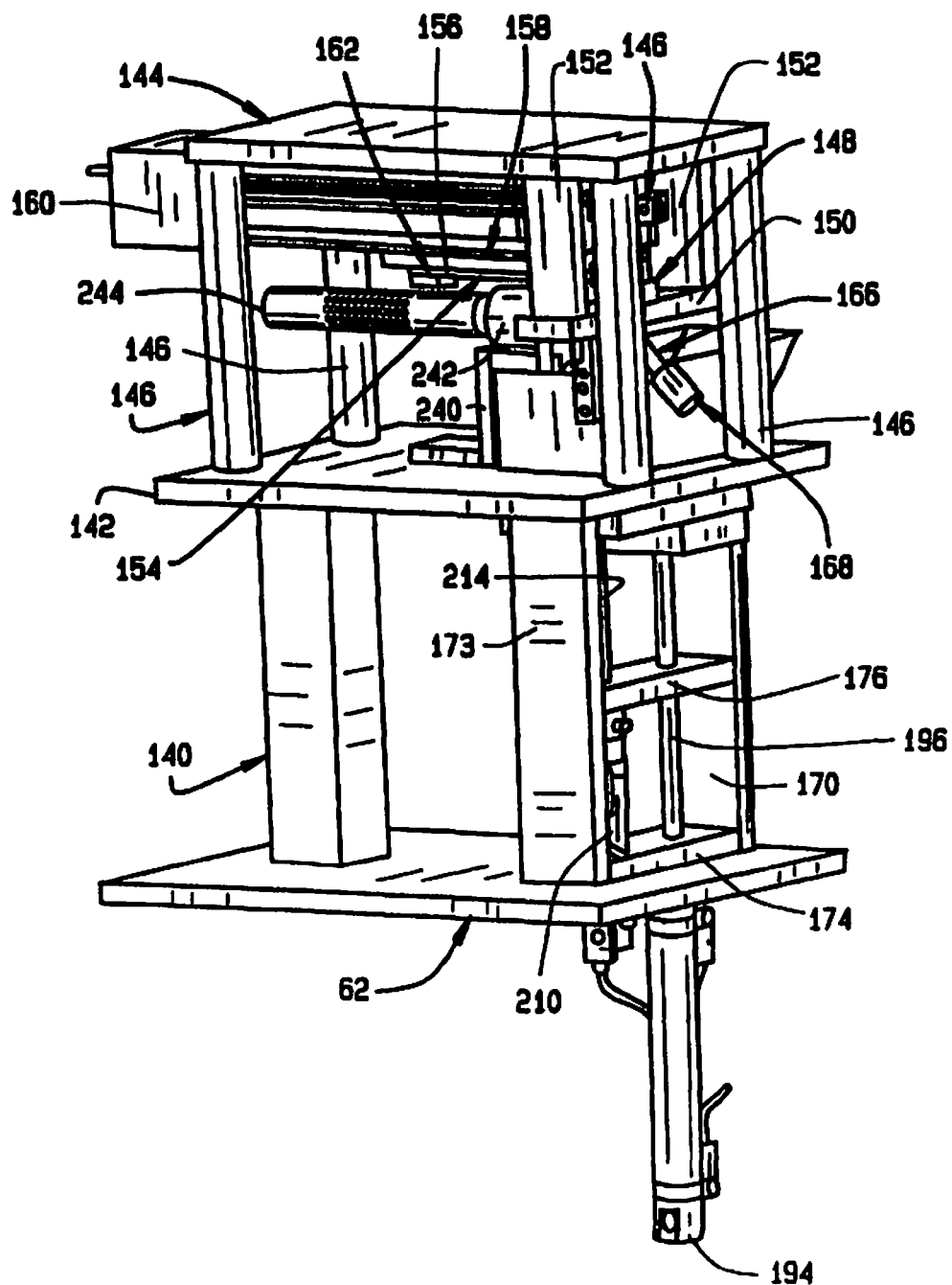
FIG. 2 is an enlarged perspective view of the seed sampler assembly of the seed sampler system.

As shown in FIGS. 1 and 2, the sampler assembly 26 is mounted on the plate 62 of the frame 24. The sample assembly comprises a bin or hopper 70, a sampling station 72, and a feed mechanism 74 for delivering a single seed from the hopper 70 to the sampling station.

Figure 3:
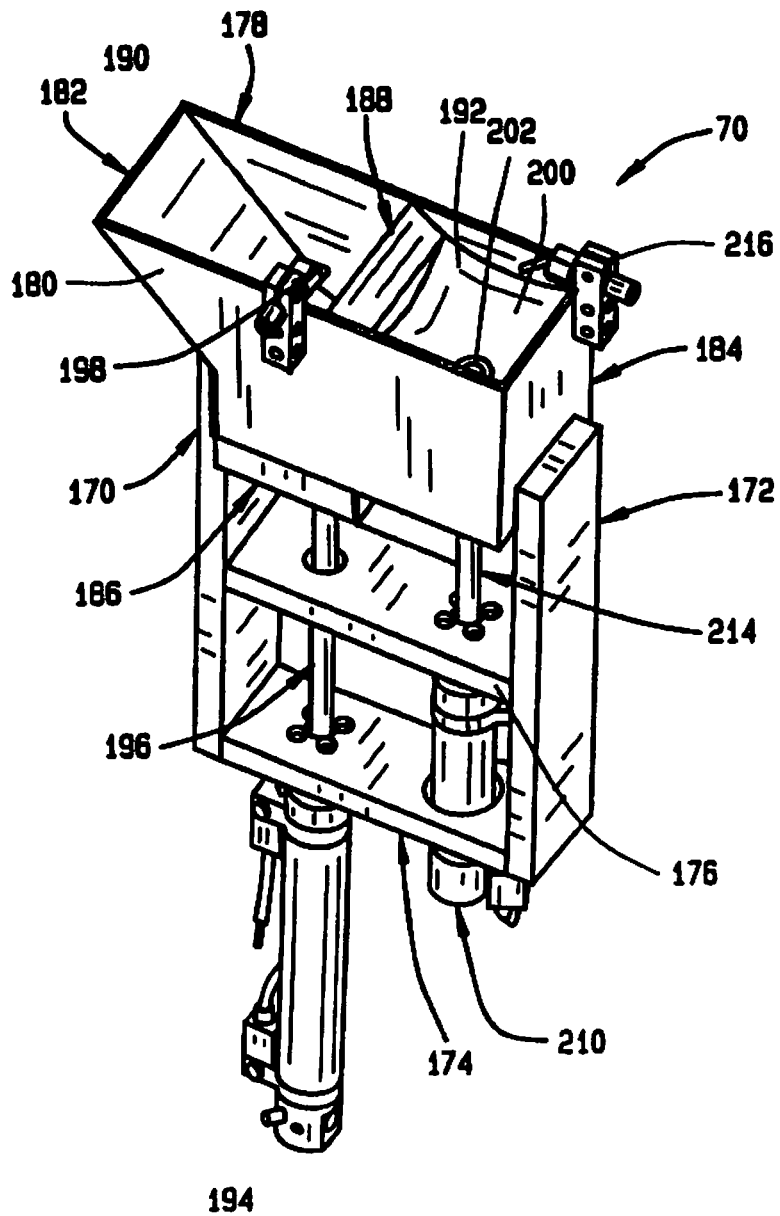
FIG. 3 is an enlarged perspective view of the hopper and seed feeding mechanism of the seed sampler assembly.

As shown in FIGS. 1 and 3, the stage 28 is adapted to securely mount a plurality of seed trays 80 and sample trays 82 in fixed positions and orientations. Each of the seed trays 80 and sample trays 82 is preferably divided into a plurality of compartments. The number and arrangement of the compartments in the seed trays 80 preferably corresponds to the number and arrangement of the compartments in the sample trays 82. This facilitates the one-to-one correspondence between a seed and its sample. However, in some embodiments it may be desirable to provide multiple compartments in the sample tray for each compartment in the seed tray, for example where multiple tests may be run on the samples, or where different samples may be taken from the same seed (e.g. samples from different depths).

The stage 28 is mounted on a two-dimensional translation mechanism 30, which in this preferred embodiment comprises a base 90 with a first linear actuator 92 having a translatable carriage 94 mounted on a base 90, and a second linear actuator 96, having carriage 98 mounted on the carriage 94 of the first linear actuator 92. The stage 28 is mounted on carriage 98 of the second linear actuator 96, and thus can be moved precisely in two dimensions through the operation of the first and second linear actuators 92 and 96.

The seed conveyor 32 comprises a tube 100 with an inlet end 102 adjacent the sampling station 72, and an outlet end 104 mounted on the post 66 of the frame 24. There is a first venturi device 106 at the inlet end 102 of the tube 100 for inducing an air flow in the tube toward the outlet end 104 of the tube, and a second venturi device 108 at the outlet end 104 of the tube 100 for inducing an air flow toward the inlet end 102 of the tube. The first venturi device 106 is operated to create an air flow in the tube and draw a seed from the sampling station into the tube along the first end. The second venturi device 108 is then operated to create an air flow in the opposite direction, thereby slowing the seed down to reduce the potential for damaging the seed as it exits the outlet end 104 of the tube and is delivered to a compartment in the tray. In this preferred embodiment the second venturi 108 actually stops the movement of the seed, allowing it to drop under gravity to its compartment on a tray 80. Various position sensors can be provided on the tube 100 to detect the presence of the seed, and confirm the proper operation of the seed conveyor 32.

The sample conveyor 34 comprises a tube 120 with an inlet end 122 adjacent the sampling station 72, and an outlet end 124 mounted on the post 68 of the frame 24. There is a first venturi device 126 at the inlet end 122 of the tube 120 for inducing an air flow in the tube toward the outlet end 124 of the tube. A separator 128 is provided at the outlet end to separate the sample material from the air stream carrying it, so that the air stream does not blow the sample out of the compartment in the tray 82. The separator preferably also contains a filter to prevent cross-contamination of the samples.

As shown in FIG. 2, the seed sampling assembly 26 is adapted to be mounted on the plate 62 on a post 140. The seed sampling assembly 26 comprises a hopper mounting plate 142, a slide mounting plate 144 and four slide standoff supports 146 therebetween. The hopper 70 (shown in FIG. 3), which feeds individual seeds to a sampling station 72, is mounted on the hopper plate 142. The sampling station 72 comprises a seed nest 148 mounted on a nest mount 150, which is supported from the slide mounting plate 144 by a pair of standoffs 152. The nest 148 has a recess opening to its bottom surface, into which the hopper 70 feeds a single seed. There is a slot in the top of the seed nest 148 through which a portion of a seed in the recess is exposed. A broach 154 (FIG. 4) is mounted in a broach holder 156 which is mounted on a slide transition plate 158 on a programmable slide 160, with a broach clamping block 162. The programmable slide 160 (FIG. 5) is mounted on the underside of the slide mounting plate 144, and moves the broach 154 through the slot in the seed nest 148 to remove a sample from a seed in the recess in the seed nest.

Figure 4:
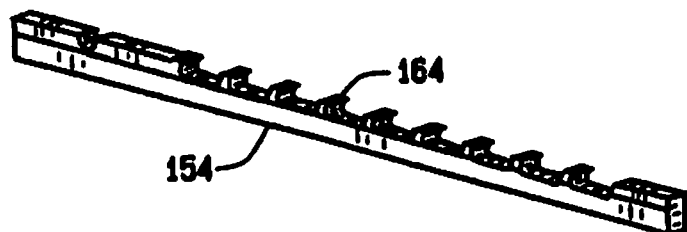
FIG. 4 is a perspective view of the broach for scraping samples from the seeds.
Figure 5:
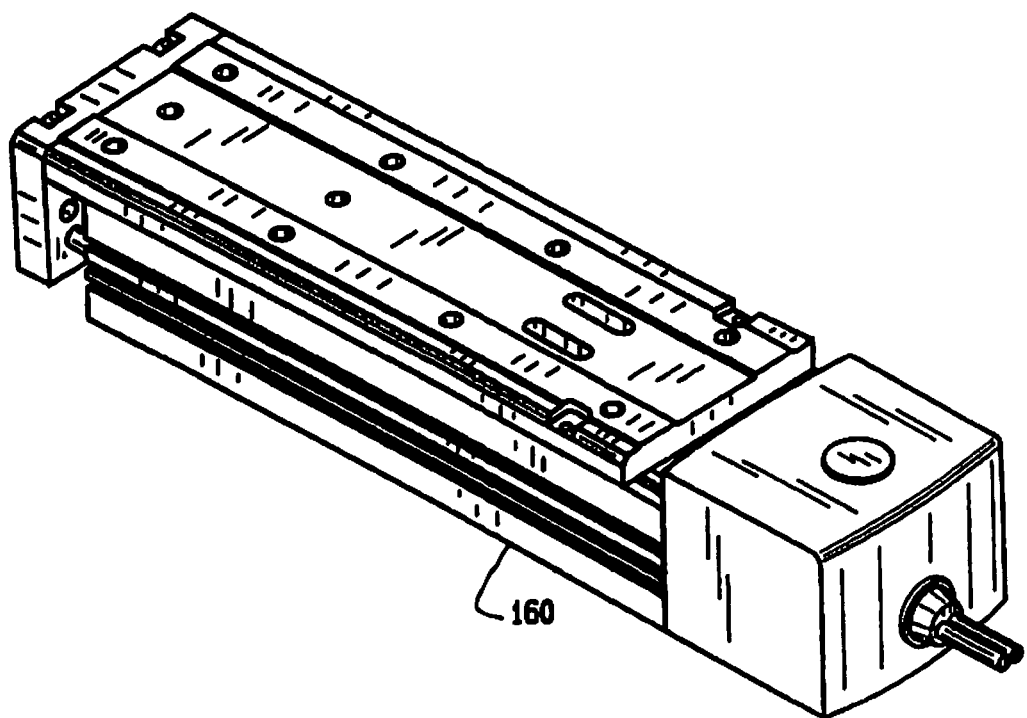
FIG. 5 is a perspective view of the slide for driving the broach.
Figure 6:
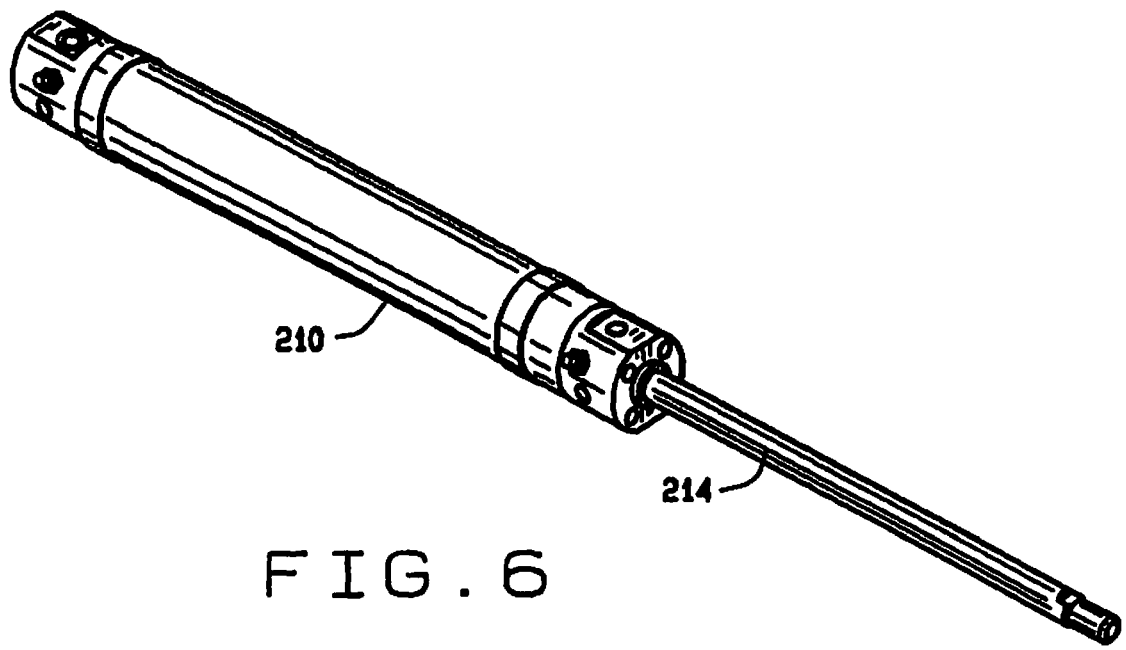
FIG. 6 is a perspective view of the piston in the feed mechanism of the hopper.

As best shown in FIG. 4 the broach 154 has a plurality of teeth 164 that increase in height toward the proximal end, so that as the broach 154 is advanced in the slot, it cuts increasingly deeper into the seed in the recess in the nest 148. The resulting gradual shaving reduces the damage to the seed, protecting its viability. Moreover, as described in more detail below, by cutting at different depths at different times, samples from different depths of the same seed can be separated for separate analysis.

A sample transfer tube 166 extends from the recess in the seed nest 148, and has a connector 168 on its end for connection to the sample conveyor 34.

The sampling station 26 also includes a hopper 70, shown best in FIG. 3. The hopper 70 comprises left and right hopper mounting plates 170 and 172, and a cylinder mounting plate 174 and a upper cylinder bracket 176. The hopper 70 also has a front panel 178, a back panel 180, first and second end panels 182 and 184, and bottom 186. A divider 188 divides the hopper into first and second compartments 190 and 192. The first compartment 190 holds a supply of seeds which are individually transferred to the second compartment 192.

A piston actuator 194 operates a piston 196 to lift a seed out of the first compartment. A air jet assembly 198 transfers a seed from the end of the piston 196 to the second compartment 192. The second compartment has a shaped bottom 200, with a well 202 for receiving the seed and positioning it. A piston actuator 210 operates a piston 214 to lift a seed out of the second compartment 192. An air jet assembly 216 is used to stir the seeds during the seed pick up procedure.

Figure 7:
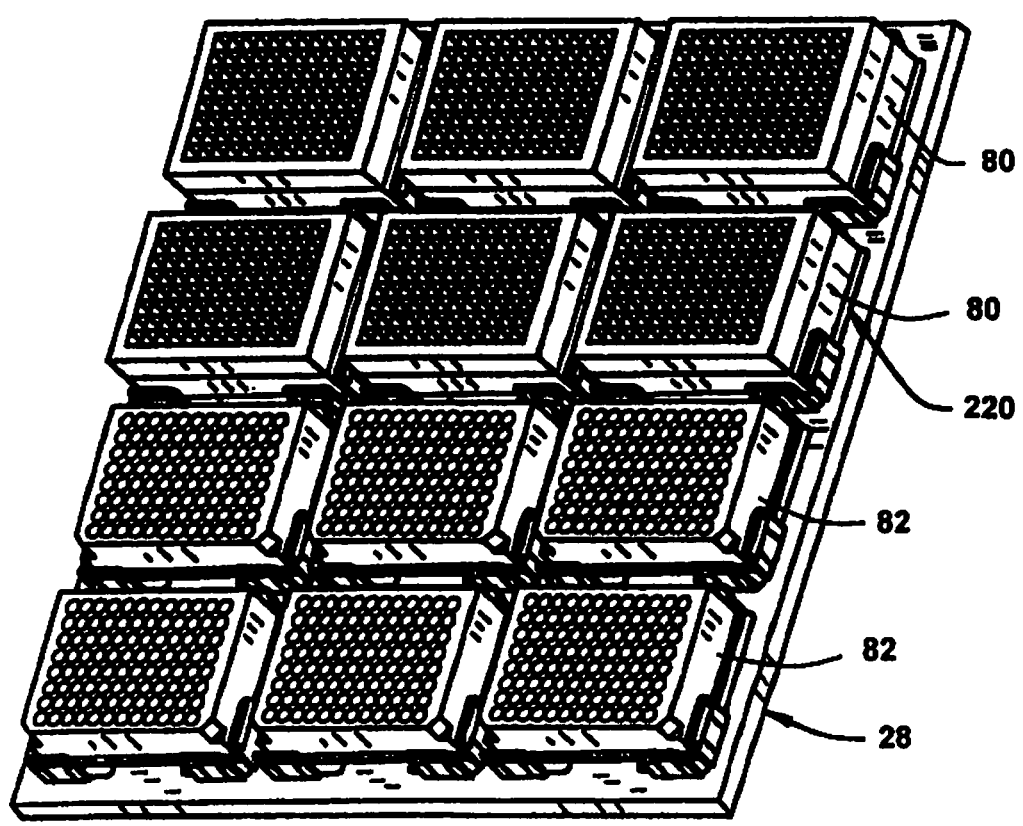
FIG. 7 is a perspective view of a stage with a plurality of seed trays and sample trays mounted thereon.

As shown in FIG. 7, the stage 28 has brackets 220 for mounting seed trays 80 and sample trays 82 in registration so that the seed conveyor and the sample conveyor deliver seeds and samples to corresponding compartments, in the respective trays. The sample trays 82 can (as shown) be adapted to hold individual vials. Of course, trays of different configurations could be used, for example where multiple compartments are provided for multiple samples from the same seed. For example where one sample is divided into several samples, or where the samples are separated from where they are taken, e.g. by depth.

Figure 8:
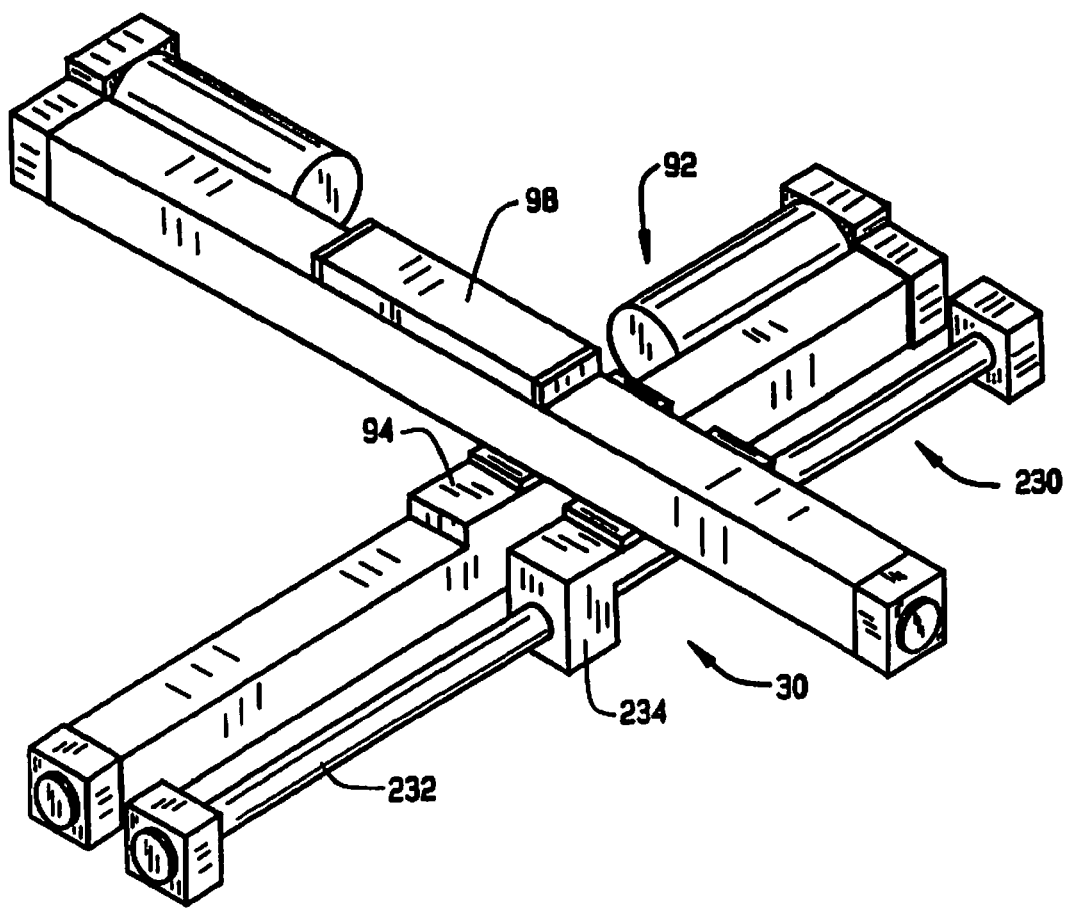
FIG. 8 is a perspective view of the two-dimensional translation mechanism.

As shown in FIG. 8, the two-dimensional translation mechanism 30 also includes a slider 230 having a rail 232 and a carriage 234, that is positioned parallel to the first linear actuator 92. The second linear actuator 96 is mounted on the carriage 94 having carriage 98 mounted on the carriage 94 of the first linear actuator 92. The stage 28 is mounted on carriage 98 of the second linear actuator 96, and thus can be moved precisely in two dimensions through the operation of the first and second linear actuators 92 and 96. Under appropriate control the translation mechanism can align individual compartments of the seed trays 80 and sample trays 82 with the outlets of the seed conveyor and sample conveyer.

Figure 12:
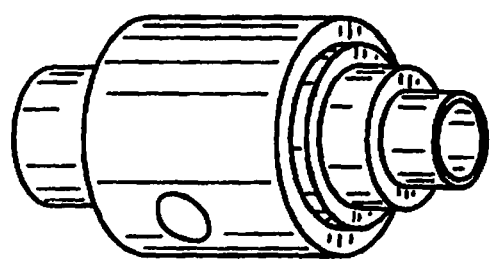
FIG. 12 is a perspective view of the air multiplier used in the seed and sample conveyors.
Figure 9:
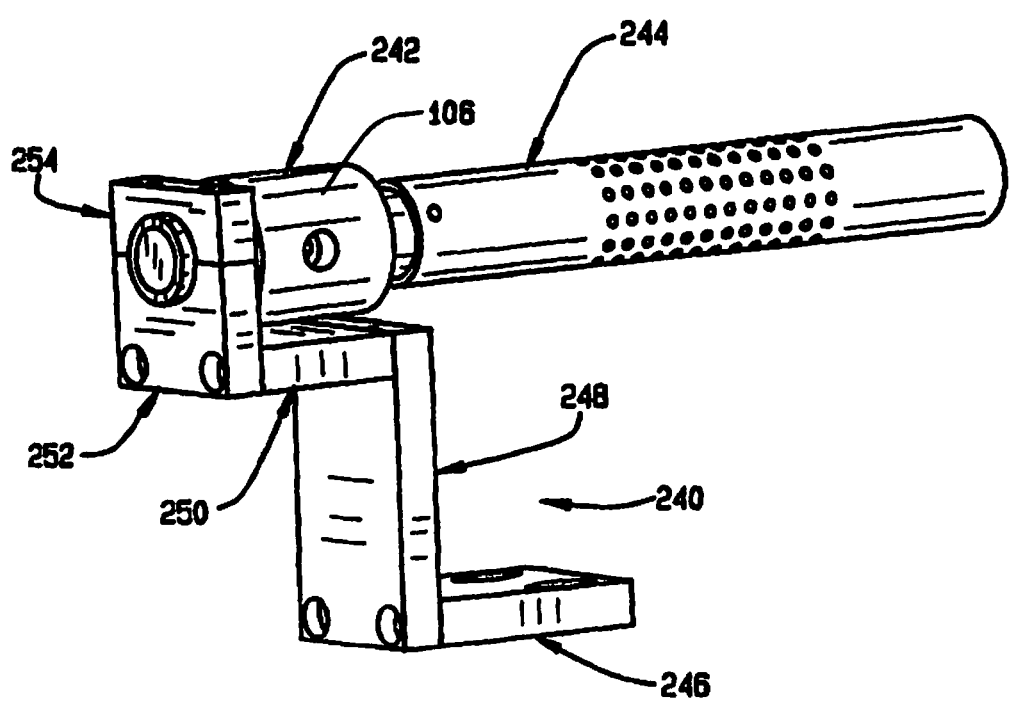
FIG. 9 is a perspective view of the inlet of the seed conveyor.

As shown in FIG. 9, at the inlet end 102 of the tube 100 of seed conveyor 32, a bracket 240 mounts an air amplifier 242 and a seed sensor tube 244. The bracket 240 comprises sections 246, 248, 250, 252 and 254. As shown in FIG. 2, the bracket 240 is mounted on the hopper mounting plate 142. The air amplifier 242 (shown in FIG. 12) is adapted to be connected to a source of compressed air. When air is applied to the air amplifier, it induces an air flow through the tube 100, employing the venturi effect. The sensor tube 244 carries seed sensors 256 for sensing the passage of a seed therethrough. The sensors 256 are preferably optical sensors aligned with openings in the sensor tube 244 which optically detect the passage of a seed.

Figure 10:
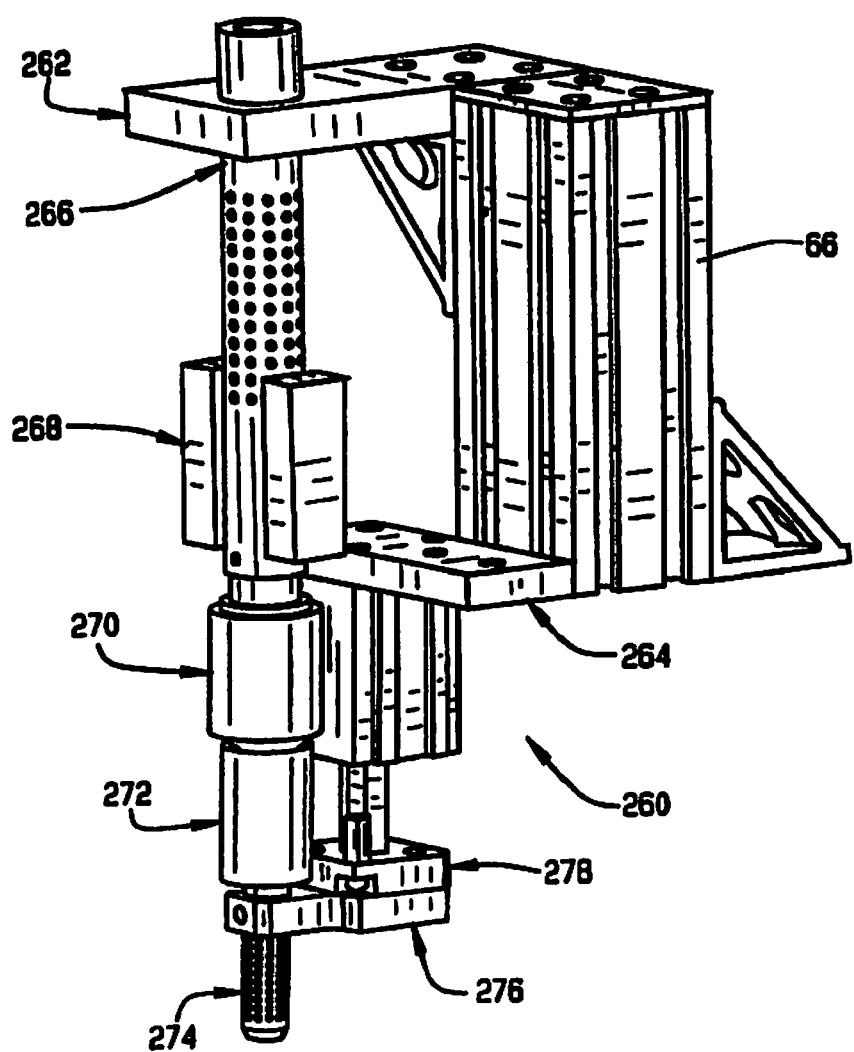
FIG. 10 is a perspective view of the outlet of the seed conveyor.

As shown in FIG. 10, a seed discharge assembly 260 is disposed at the outlet end 104 of the tube 100 of seed conveyor 32. The discharge assembly is mounted on post 66, with a bracket 262 and a discharge support 264. A seed sensor tube 266 is mounted in the bracket 262, and carries seed sensors 268 for sensing the passage of a seed therethrough. The sensors 268 are preferably optical sensors aligned with openings in the sensor tube 266 which optically detect the passage of a seed. An air amplifier 270 is connected to the seed sensor tube 266. The air amplifier 270 (FIG. 12) is adapted to be connected to a source of compressed air. When air is applied to the air amplifier, it induces an air flow through the tube 100, employing the venturi effect. Below the air amplifier 270 is a connector tube 272, and below that is a vented seed discharge tube 274, which is also supported by a seed discharge tube holder 276, carried on a seed discharge tube actuator 278.

Figure 11:
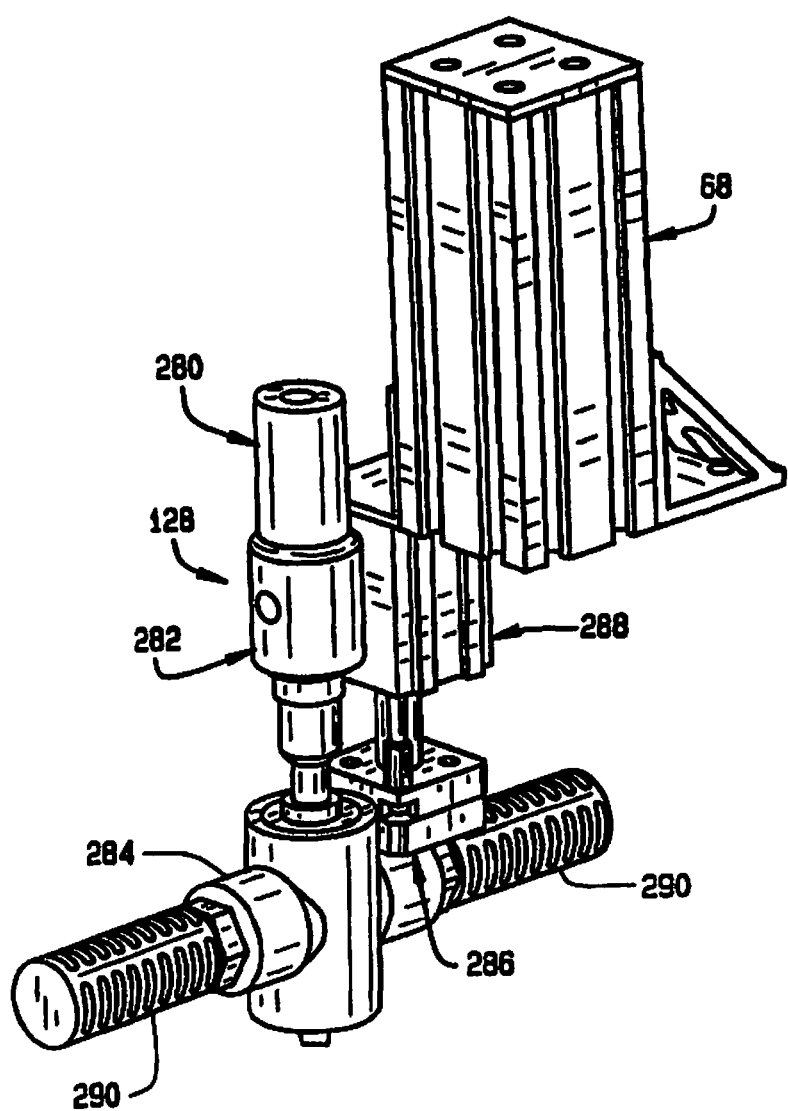
FIG. 11 is a perspective view of the outlet of the sample conveyor.
Figure 15:
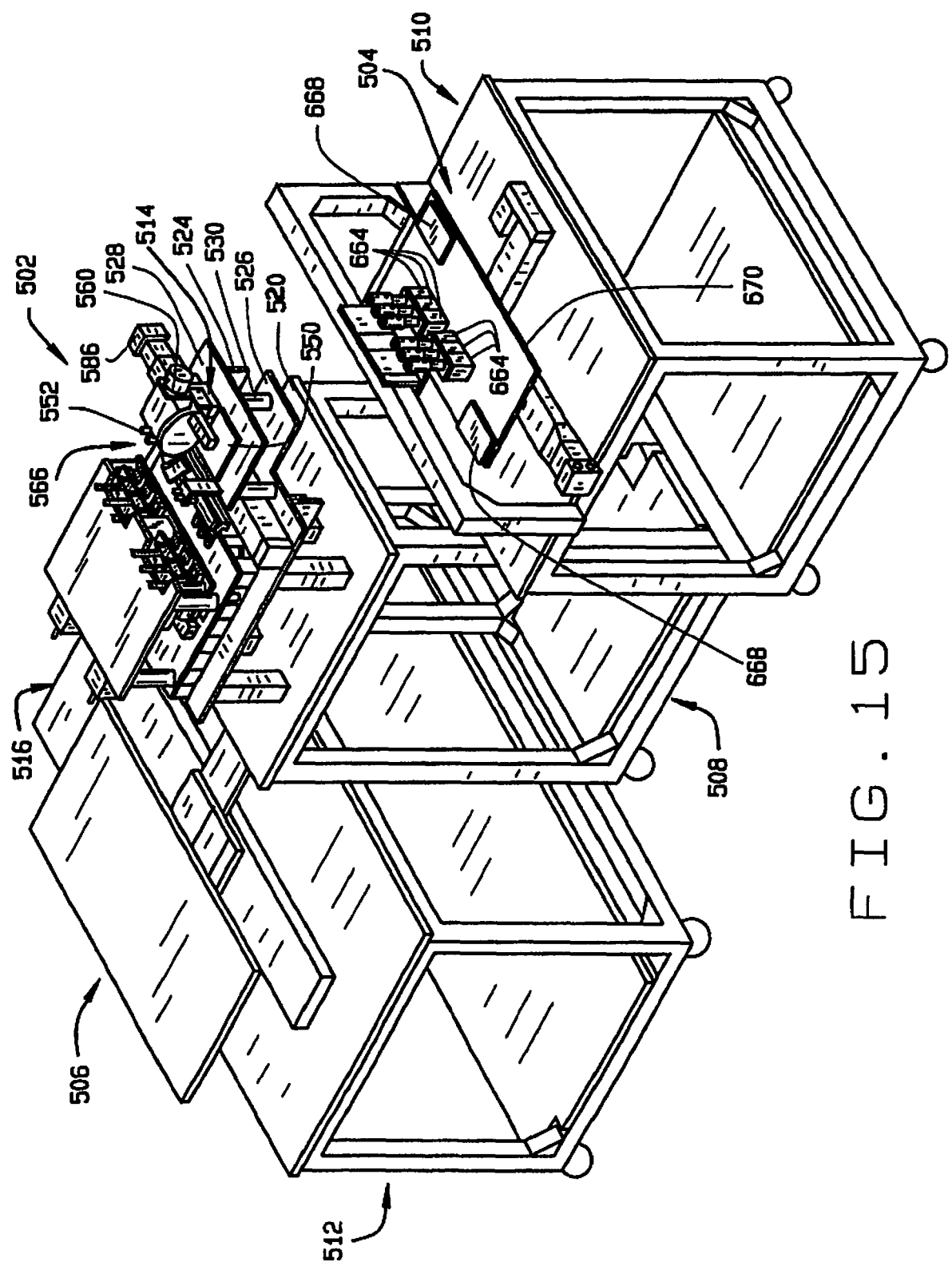
FIG. 15 is a front perspective view of the seed sampler system.
Figure 16:
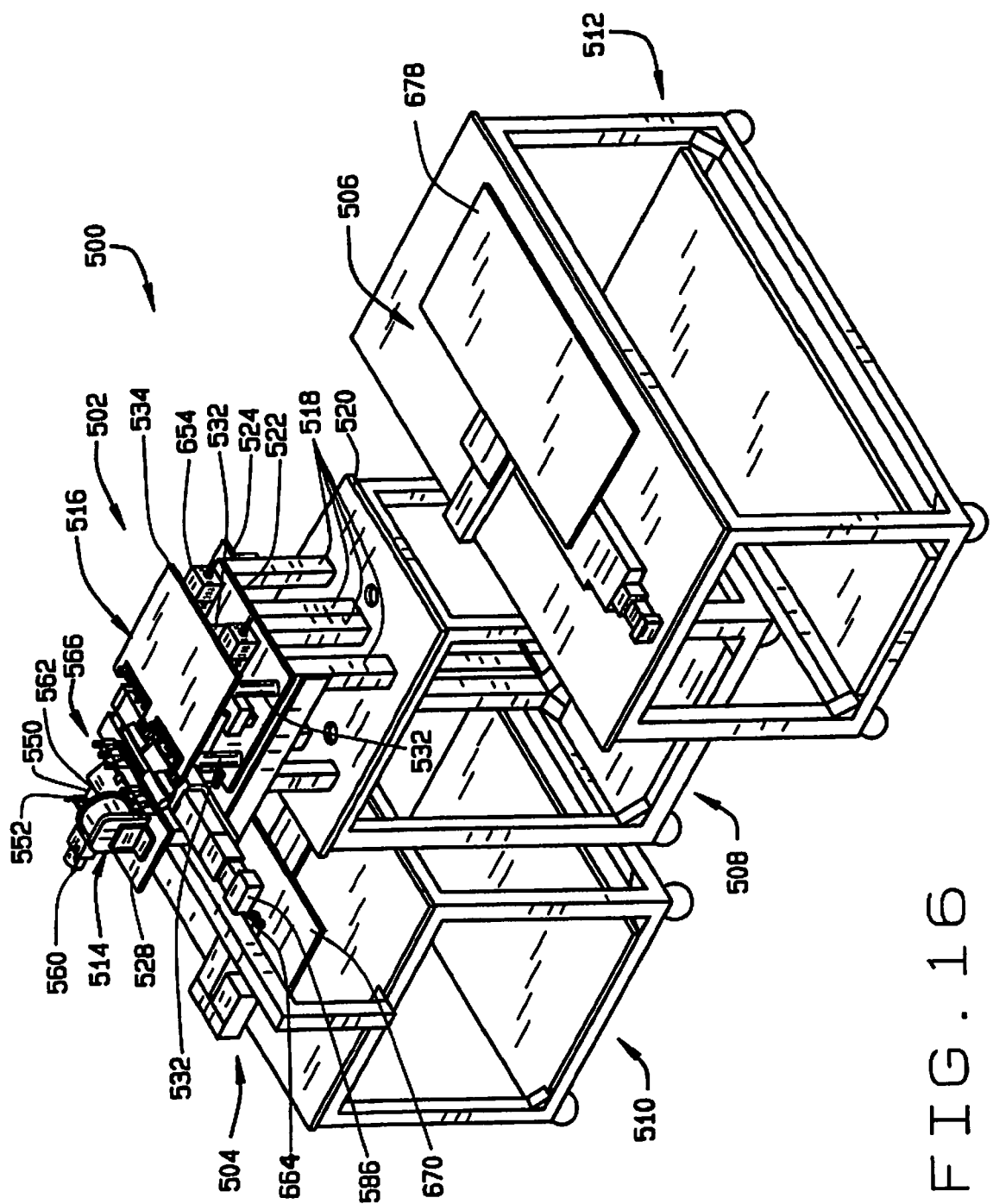
FIG. 16 is a rear perspective view of the seed sampler system.
Figure 17:
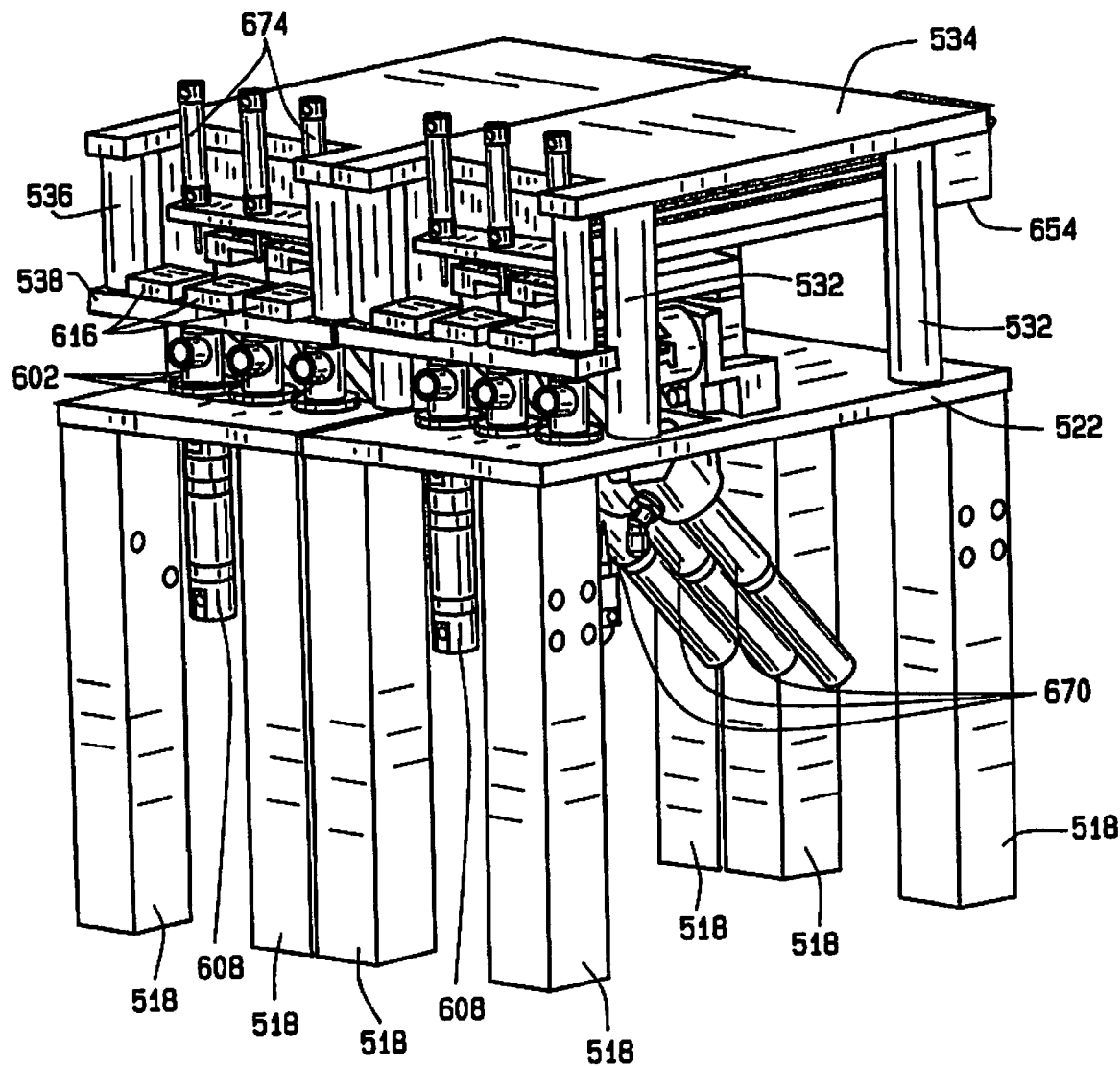
FIG. 17 is a perspective view of the sampling station of the high throughput seed sampler system.
Figure 18A:
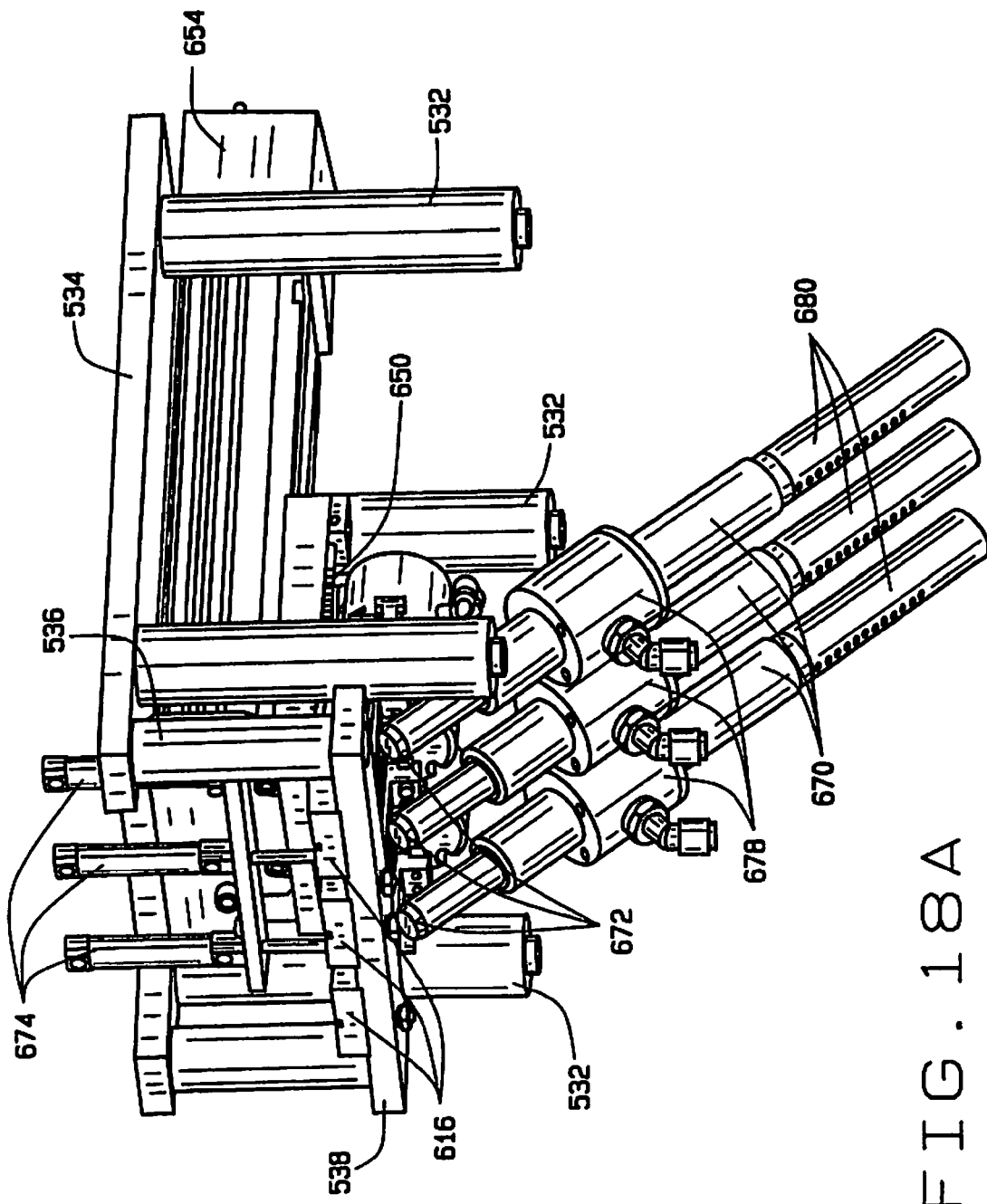
FIG. 18A is a partial perspective view of one portion of the seed sampling station in accordance with the principles of this disclosure, with the broach retracted.
Figure 18B:
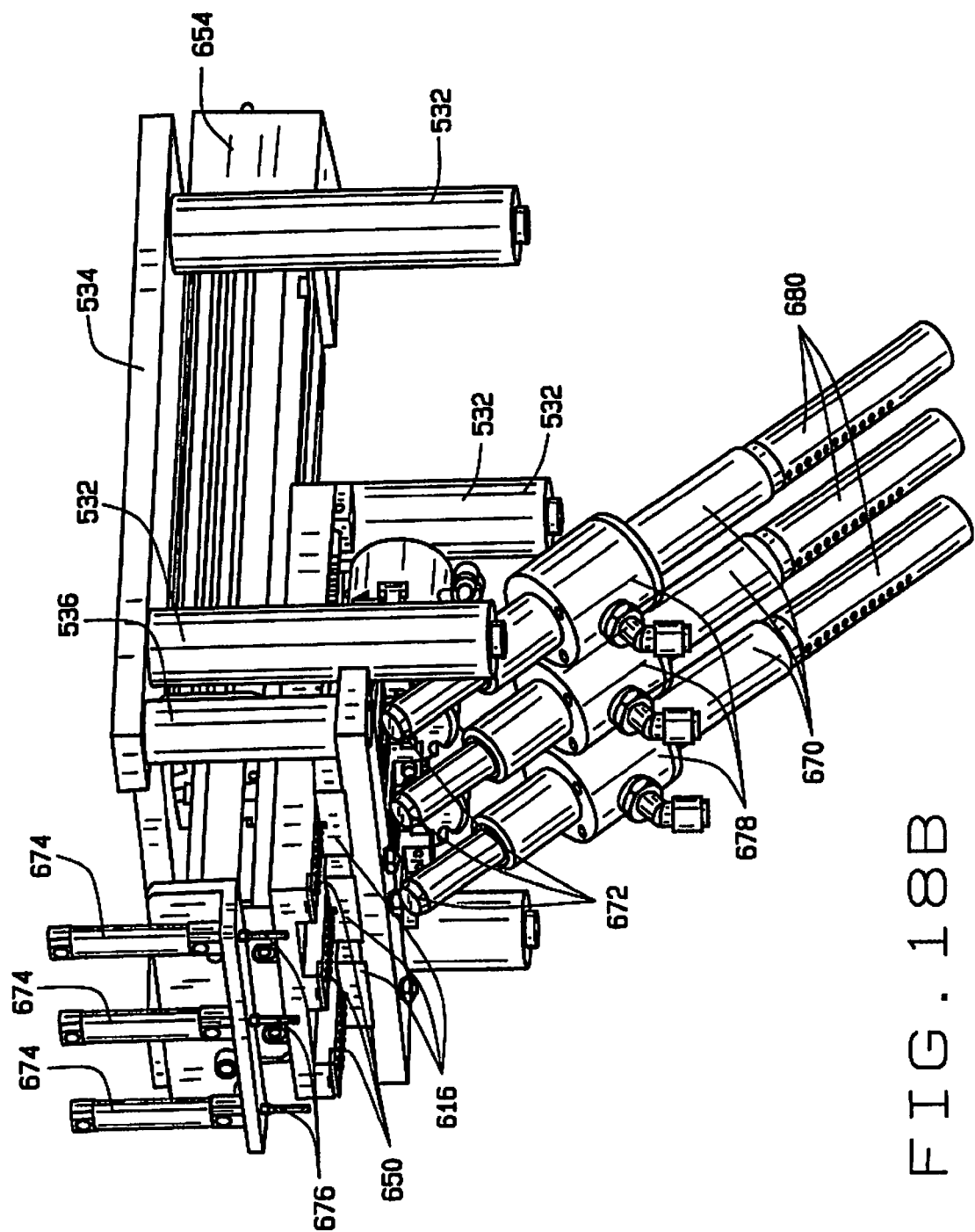
FIG. 18B is a partial perspective view of one portion of the seed sampling station in accordance with the principles of this disclosure, with the broach extended.

The inlet end 122 of the tube 120 of the sample conveyor 34 is connected via connector 168 to the sample discharge tube 166. As shown in FIG. 11, the outlet end 124 of the tube 120 is connected to a sample connector 280, which in turn is connected to air amplifier 282, which is connected to chip nozzle assembly 284. The chip nozzle assembly 284 is mounted on the seed discharge tube holder 286, which is carried on a discharge actuator 288. The discharge actuator is mounted on the post 68. Filters 290 are mounted on the outlets of the chip nozzle assembly 284, to prevent samples being discharged from contaminating the other compartments.

Operation of the Sampler System

In operation, a plurality of seeds, for example soybeans, are deposited in the hopper 70. The seed feed mechanism 74 conveys an individual seed to the sampling station 72. At the sampling station, a sample of material is removed from the seed in a manner that minimizes the impact to the viability of the seed.

The sample is removed from the sampling station 72 by the sample conveyor 34. The venturi device 126 creates an air flow in the tube 120 toward the outlet end 124. The sample material is drawn into the tube and toward the compartment of the sample tray aligned with outlet end 124 of the tube 120. The separator 128 separates the sample from the air stream carrying it, and allows the sample to drop into the compartment. In some embodiments, the sample may be distributed to two or more compartments in the sample tray, in which case the two-dimensional translation mechanism 30 is operated to bring one or more additional compartments into alignment with the outlet 124. It is possible to accurately coordinate the movement of the sample trays with the operation of the sampling station 72 so that samples from different portions of the seed, and in particular different depths of the seed, can be delivered to separate compartments in the sample tray.

After the sampling from the seed is completed, the seed conveyor 32 is operated to remove the seed from the sampling station. The first venturi device 106 is operated to create an air flow in the tube and draw a seed from the sampling station 72 into the tube 100. The second venturi device 108 is then operated to create an air flow in the opposite direction, thereby slowing the seed down to reduce damage to the seed as it exits the outlet end 104 of the tube 100 and is delivered to a compartment in the seed tray 82. The second venturi 108 preferably stops the movement of the seed, allowing it to drop under gravity to its compartment on a tray 80. The operation of the first and second venturis 106 and 108 can be timed, or they can be triggered by position sensors monitoring the tube 100.

An embodiment of a high throughput seed sampler system is indicated generally as 500 in FIGS. 13-26. As shown in FIGS. 13 and 14, the seed sampler system 500 comprises a sampling station 502, a sample handling station 504, and a seed handling station 506. It is desirable, but not essential, that the seed sampler system 500 fit on one or more wheeled carts that can pass though conventional doorways, so that the system can be conveniently transported. In this preferred embodiment, the seed sampling station 502 is mounted on a cart 508, the sample handling station is mounted on a cart 510, and the seed handling station is mounted on a cart 512.

The seed sampling station 502 comprises a seed feeder 514 and a seed chipper 516. A plurality of columns 518 extend vertically upwardly from the surface 520 of the cart 508. A platform 522 is mounted on top of columns 518 and supports the seed chipper 514. Two L-brackets 524 extend horizontally from the columns 518, and support a platform 526. A stage 528 is mounted on the platform 526 by a plurality of posts 530 and supports the seed feeder 514.

A plurality of pillars 532 extend upwardly from the plate 522. A plate 534 is mounted on the pillars 532. A plurality of posts 536 depend from the plate 534, and support a shelf 538.

Figure 23A:
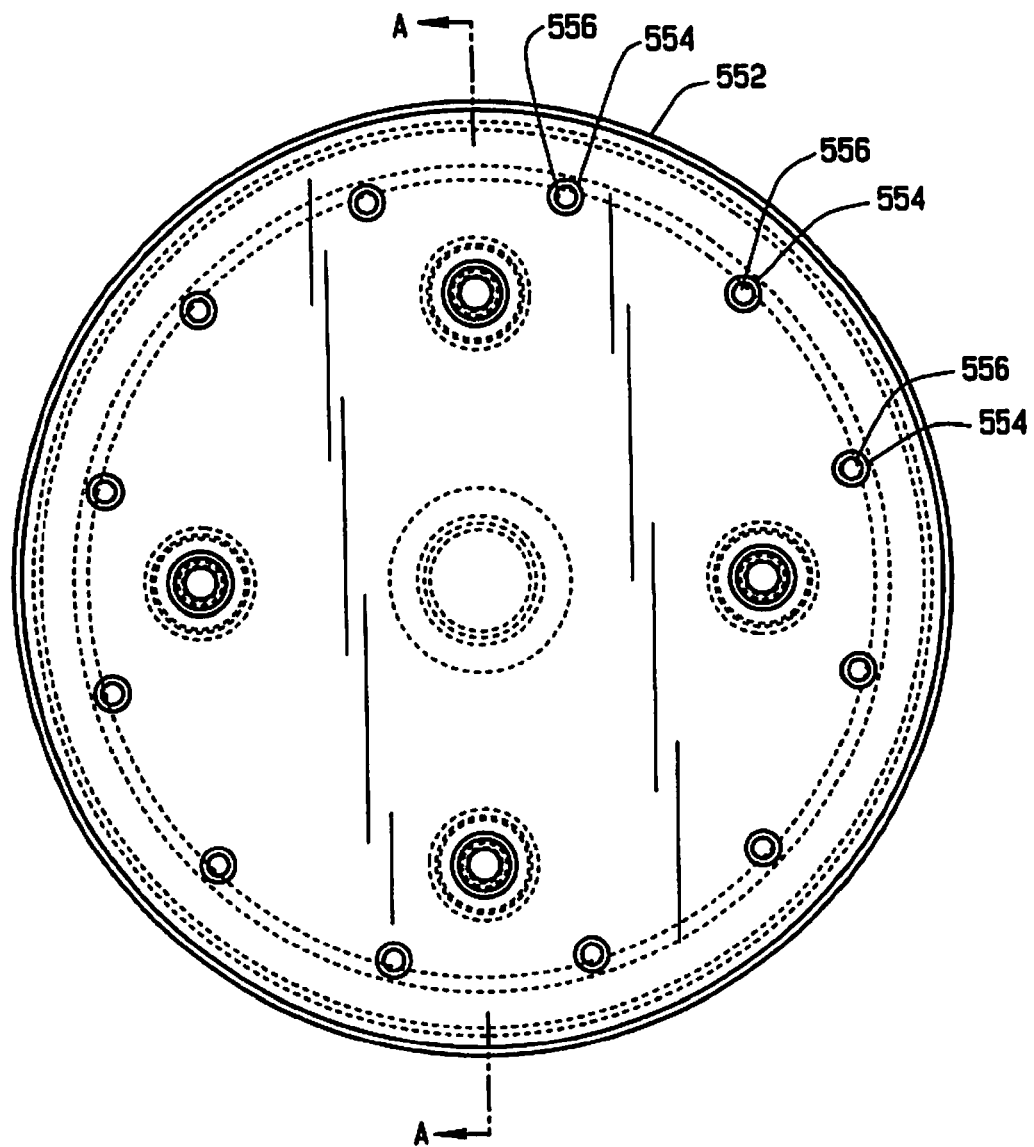
FIG. 23A is a side elevation view of the seed selecting wheel.
Figure 23B:
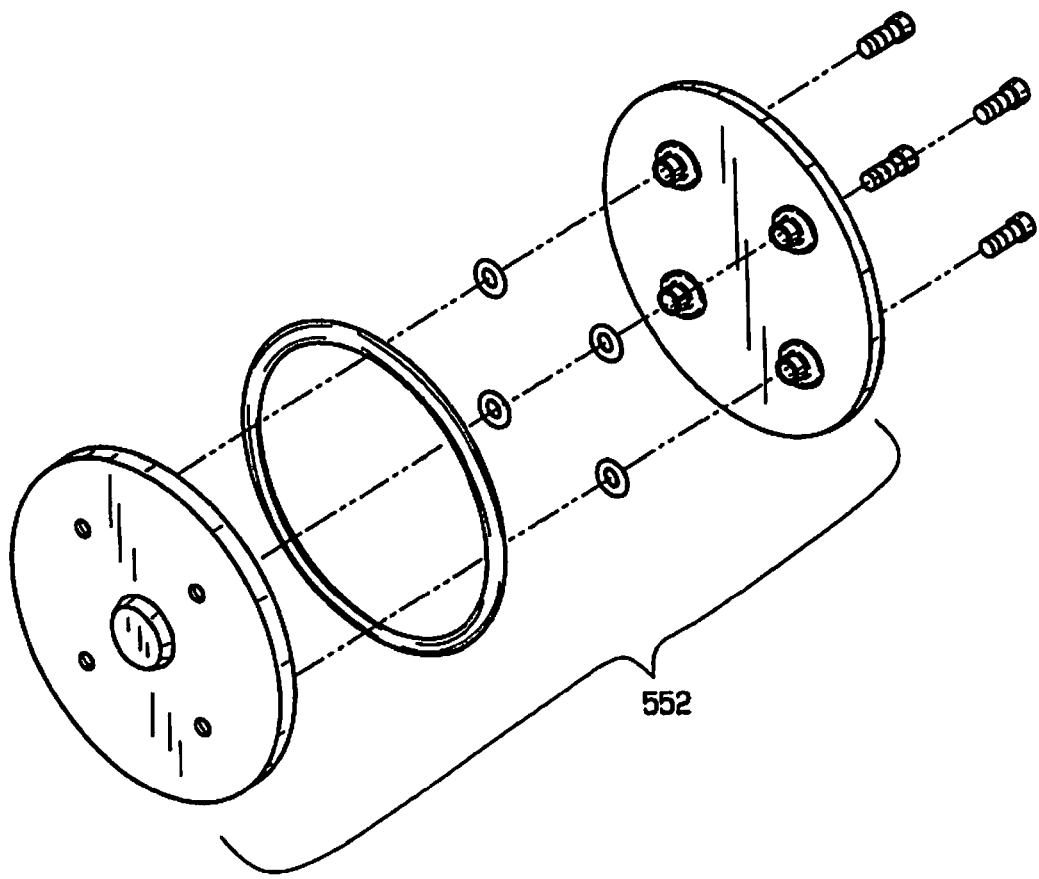
FIG. 23B is an exploded view of the seed selecting wheel.
Figure 23C:
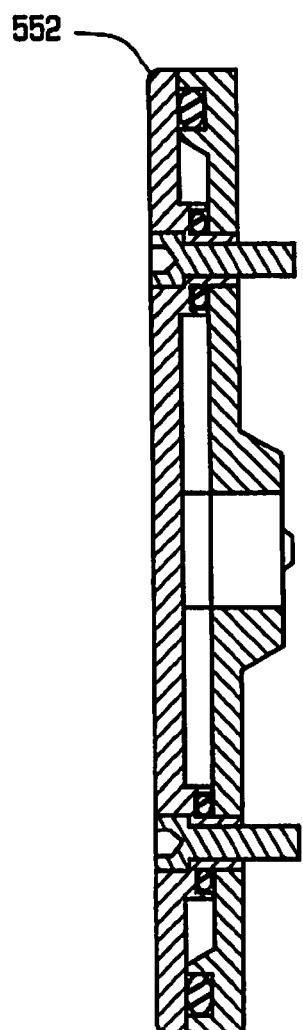
FIG. 23C is a vertical cross sectional view of the seed selecting wheel.

As shown in FIGS. 13, 14, 15 and 16, the seed feeder 514 comprises a hopper 550, with a shaped surface adapted to feed seeds deposited into the hopper toward a separating wheel 552 (see also FIGS. 23A through 23C). The separating wheel 552 is mounted for rotation in a vertical plane adjacent the hopper 550, and has a plurality of spaced recesses 554 each having an opening 556 therein communicating with a vacuum system (not shown). The wheel 552 is advanced with an indexing motor 560. Individual seeds are picked up by the recesses 554 in the wheel 552 and held in the recesses by suction from the vacuum system via openings 556. A wiper 562 wipes individual seeds from the recesses 554, allowing them to drop through a guide 564 into an opening in a distributor 566.

Figure 24:
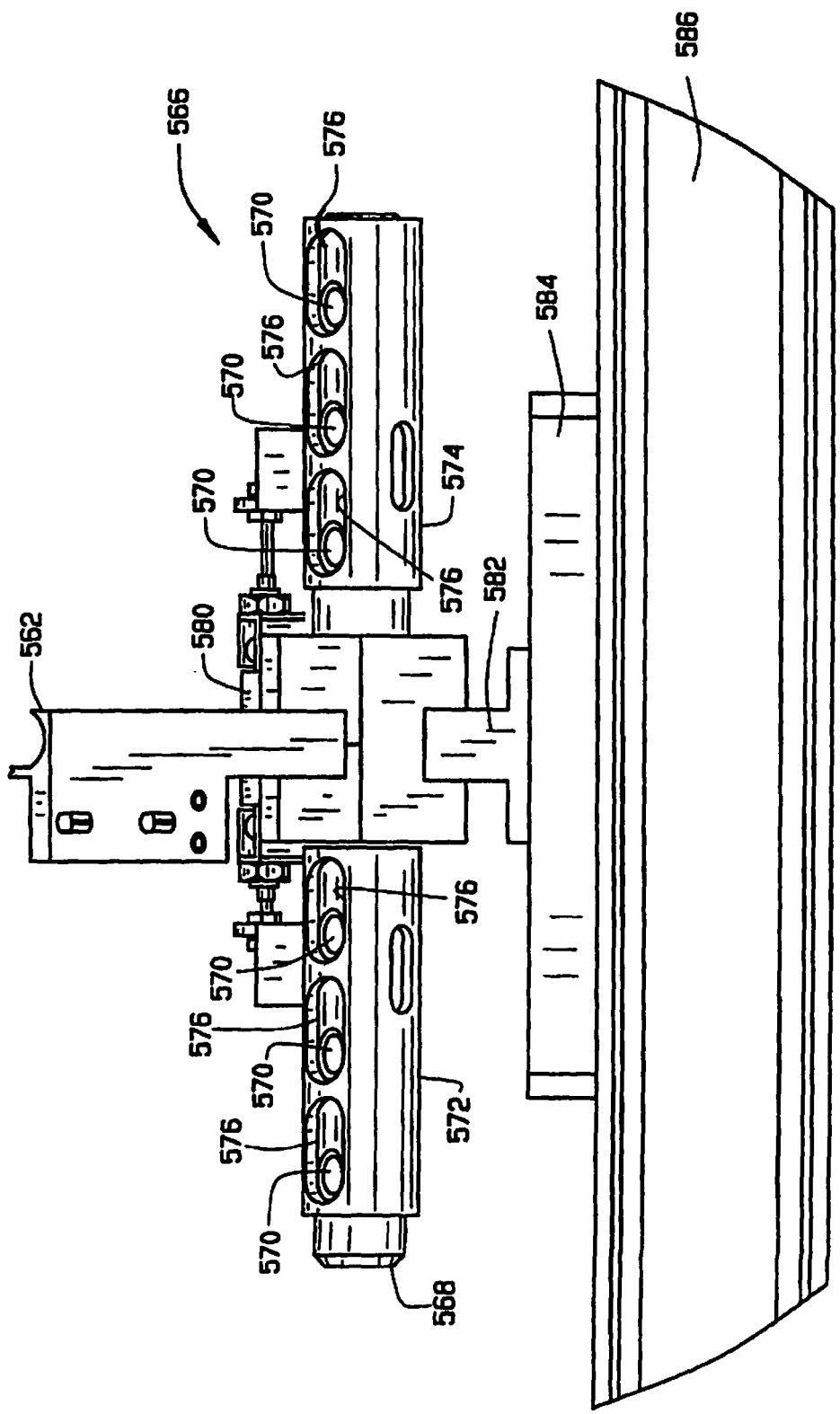
FIG. 24 is a front elevation view of the feeding mechanism.
Figure 25:
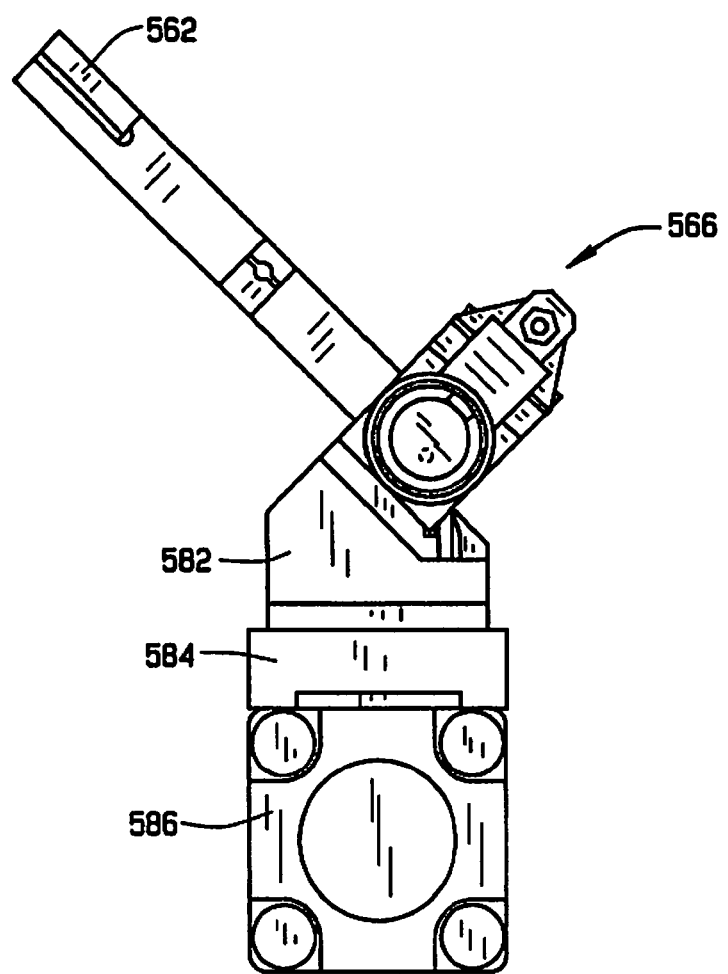
FIG. 25 is a side elevation view of the feeding mechanism.
Figure 26A:
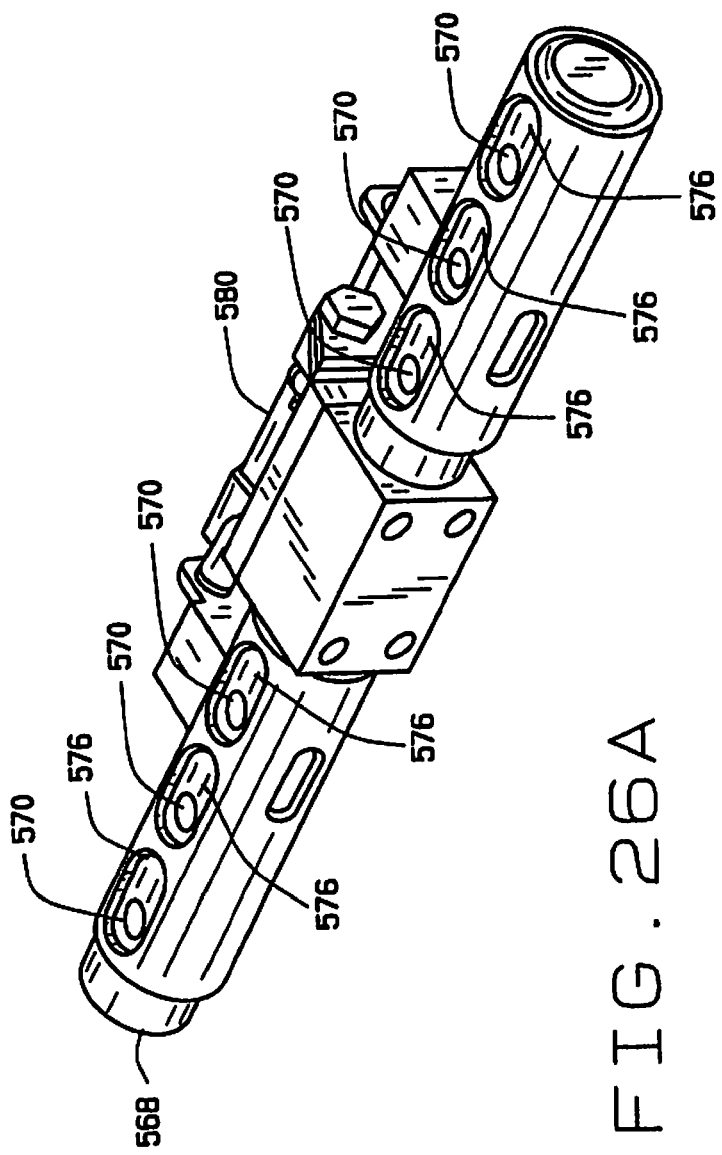
FIG. 26A is a perspective view of the feeding mechanism.
Figure 27A:
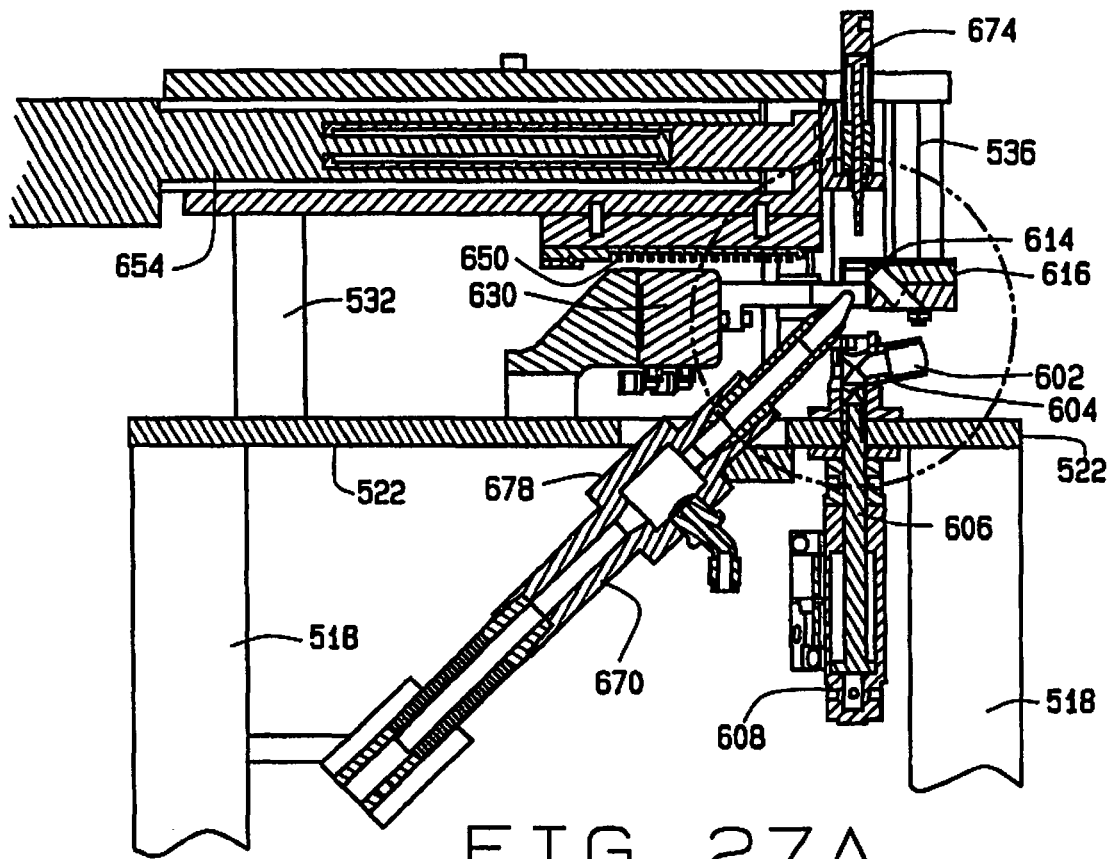
FIG. 27A is a vertical longitudinal cross-sectional view of the sampling mechanism.
Figure 27B:
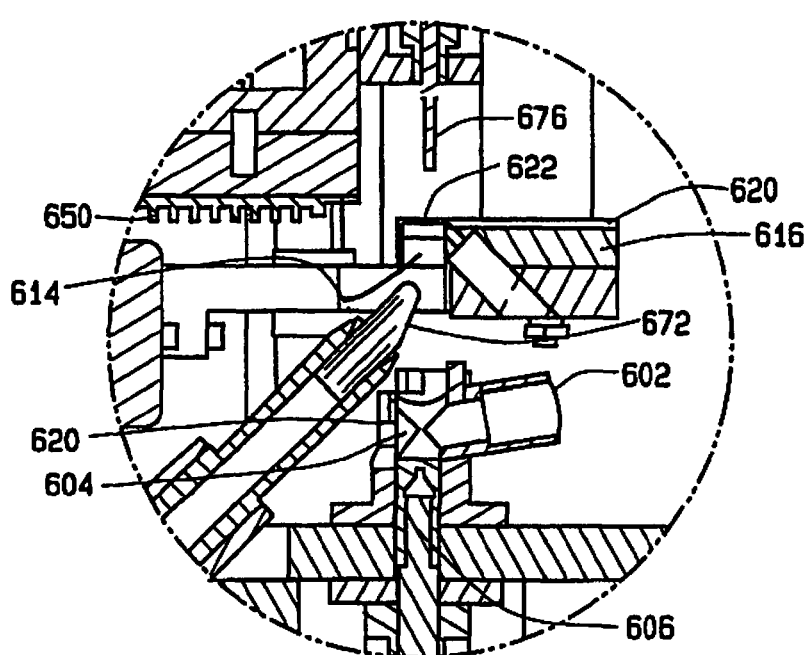
FIG. 27B is an enlarged partial vertical cross sectional view of the sampling mechanism as shown in FIG. 27A.
Figure 28A:
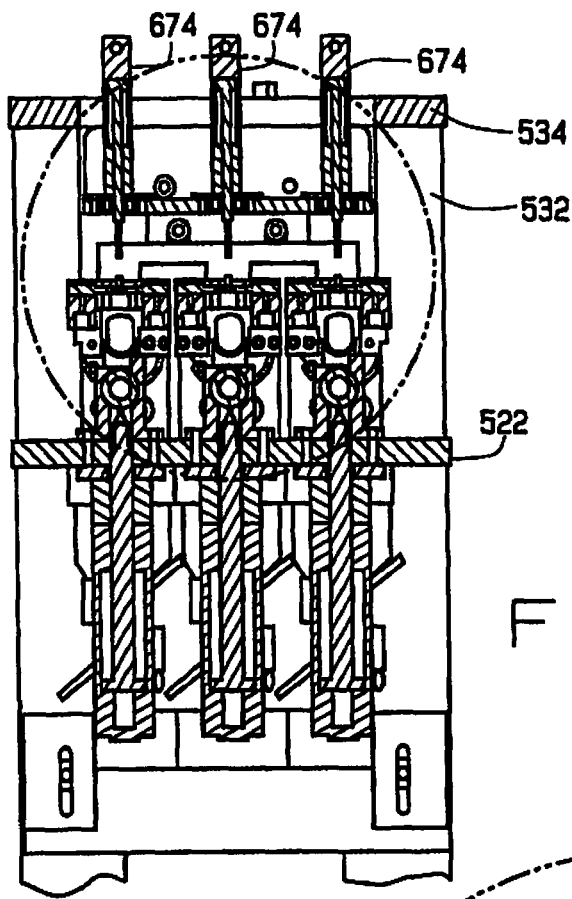
FIG. 28A is a vertical transverse cross-sectional view of the sampling mechanism.
Figure 28B:
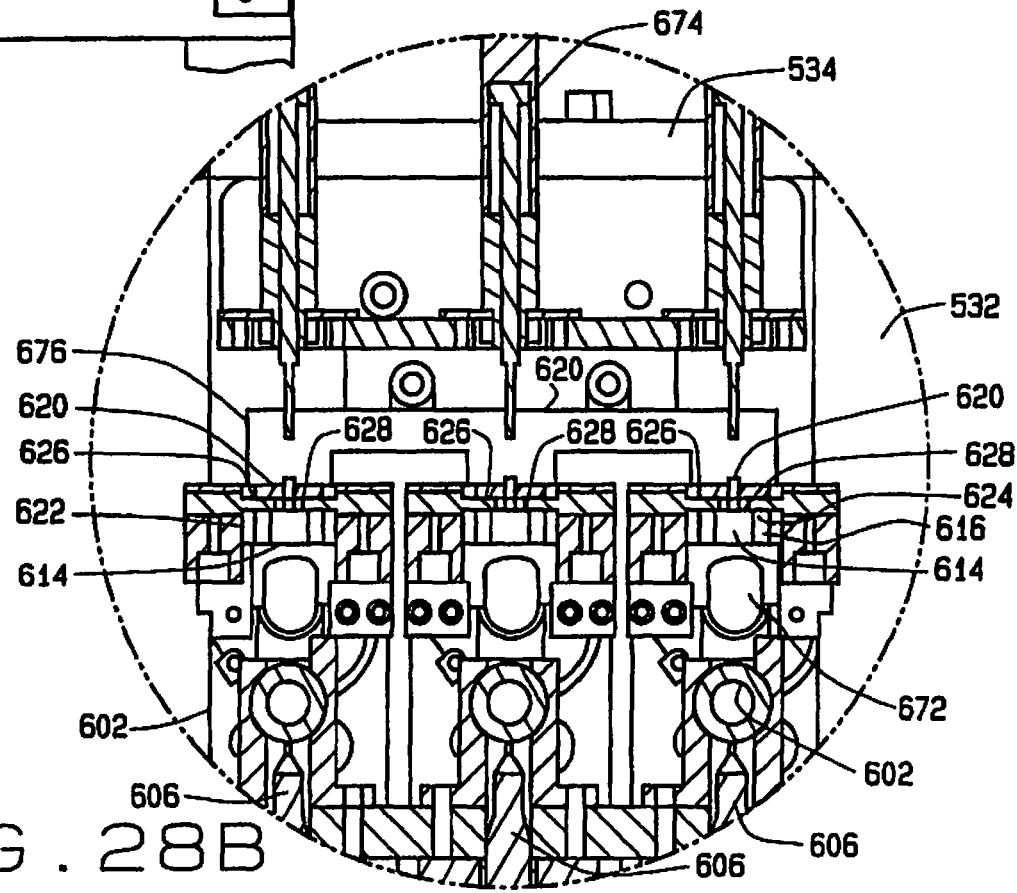
FIG. 28B is a enlarged partial cross-sectional view of the sampling mechanism as shown in FIG. 28A.

As shown in FIGS. 24-26, the distributor 566 comprises a shaft 568 having a plurality (six in the preferred embodiment) of passages 570 extending transversely there through. Sleeves 572 and 574 are slidably mounted over each end of the shaft 568 to translate between first (inboard) and second (outboard) positions. The sleeves 572 and 574 have a plurality of pairs of aligned openings 576 and 578 on opposite sides thereof. The openings 576 are elongate, and the openings 576 and 578 are sized and arranged so that when the sleeves 572 and 574 are in their first (inboard) position (on the left side in FIG. 24), a portion of the elongate openings 576 is aligned with a passage 570 in the shaft 568, and when the sleeves are in their second (outboard) positions a portion of the elongate openings 576 and the second openings 578 are aligned with the passage (on the right side in FIG. 24). An actuator 580 selectively slides the sleeves 572 and 574 between their first and second positions.

The distributor 566 is mounted by a bracket 582 on the carriage 584 of a linear actuator 586, to translate relative to the guide 564, successively bringing each of the passages 570 in the shaft 568 into alignment with the guide 564 so that a seed can be deposited therein. A seed sensor (not shown) can be mounted adjacent the guide 564 to confirm that a seed is deposited in each passage 570. A plurality of air nozzles 590 are mounted on the stage 528, and are aligned with the passages 570 when the distributor 566 is moved to its dispensing position by the actuator 586. A tube 592 is aligned with each passage 570, and each tube connects to one of a plurality of seed sampling stations 600 in the seed chipper 516. The sleeves 572 and 574 are translated allowing the seeds in the passages 570 to drop into tubes 592. One of the nozzles 590 is aligned with each of the passages 570, and is actuated to facilitate the movement of the seeds from the passages 570 through the tubes 592 to their respective seed sampling stations 600.

There is preferably a port 596 through the hopper 550 that aligns with the opening 556 in each recess 554 as the wheel 552 turns. The port 596 can be connected to a vacuum to draw any dirt or pieces of seed husks or seed that might clog the openings 556 in the recesses 554, and impair the ability of the wheel 552 to select individual seeds from the hopper 550.

The seed chipper 516 comprises at least one, and in this preferred embodiment six, sampling stations 600. Each seed sampling station 600 removes a sample of material from a seed delivered to it. In this preferred embodiment the sampling stations 600 are arranged or ganged in two groups of three, but the number and arrangement of the sampling stations could vary. The sample handling station 504 receives tissue samples removed from a seed and transported away from each sampling station 600. Similarly, the seed handling station 506 receives a seed after the sample has been removed from the seed, and the seed is transported from the sampling station 600.

Each seed sampling station 600 has an inlet collar 602 connected to the tube 592, that opens to a chamber 604. The bottom surface of the chamber 604 is formed by the end of a rod 606 of actuator 608. The surface of the bottom is below the inlet collar 602 to ensure that the entire seed drops into the chamber 604 and is not caught in a position only partly in the chamber. A vent 610 may be positioned opposite from the inlet collar 602 to allow air from air nozzles 590 to escape. The vent 610 can be covered with a mesh grille 612 to prevent the seed from escaping the chamber 604 and to cushion the seed as it is delivered into the chamber.

This rod 606 lifts a seed out of the chamber 604 and into a seed-receiving recess 614 in the underside of a seed sampling plate 616. The sampling plate 616 has a sampling opening 618 through which a seed in the seed-receiving recess 614 protrudes. A sampling groove 620 is formed in the top surface of the sampling plate 616 such that a portion of a seed in the recess 614 protrudes into the groove. The sampling plate 616 also has laterally oriented openings 622 and 624 therein aligned with the seed-receiving recess 614. When the rod 606 lifts a seed delivered to the sampling station 600 into the recess 614 in the plate 616, fingers 626 and 628 extend transversely through the openings 622 and 624 and are operated by actuator 630 to engage and compress the seed. It has been discovered that compressing at least certain types of seeds during the sampling process can improve viability of the seeds after sampling. For seeds such as soybean seeds, it has been found that a compressive pressure enhances seed viability, and that compressive pressure of between about 2.5 and about 5 pounds is sufficient to enhance viability.

A sampling broach 650 having a plurality of cutting edges 652 reciprocates in the groove 620 so that the cutting edges 652 can scrape a sample from a seed being held in the recess 614 by the rod 606 and the fingers 626 and 628. The cutting edges 652 are preferably parallel, and oriented an oblique angle less than 90° relative the direction of travel of the broach. It is desirable, but not essential, that the cutting edges 652 be angled sufficiently that one edge remains in contact with the seed at all time. Angling the cutting edges allows the next blade to establish contact with the seed before the current blade loses contact with the seed. In the preferred embodiment the cutting edges are oriented at an angle of about 60°, although this angle will depend somewhat upon the width of the broach. The width of the broach can also be important to preserving seed viability after sampling, and may vary depending upon the type of seed and its moisture content.

Figure 19A:
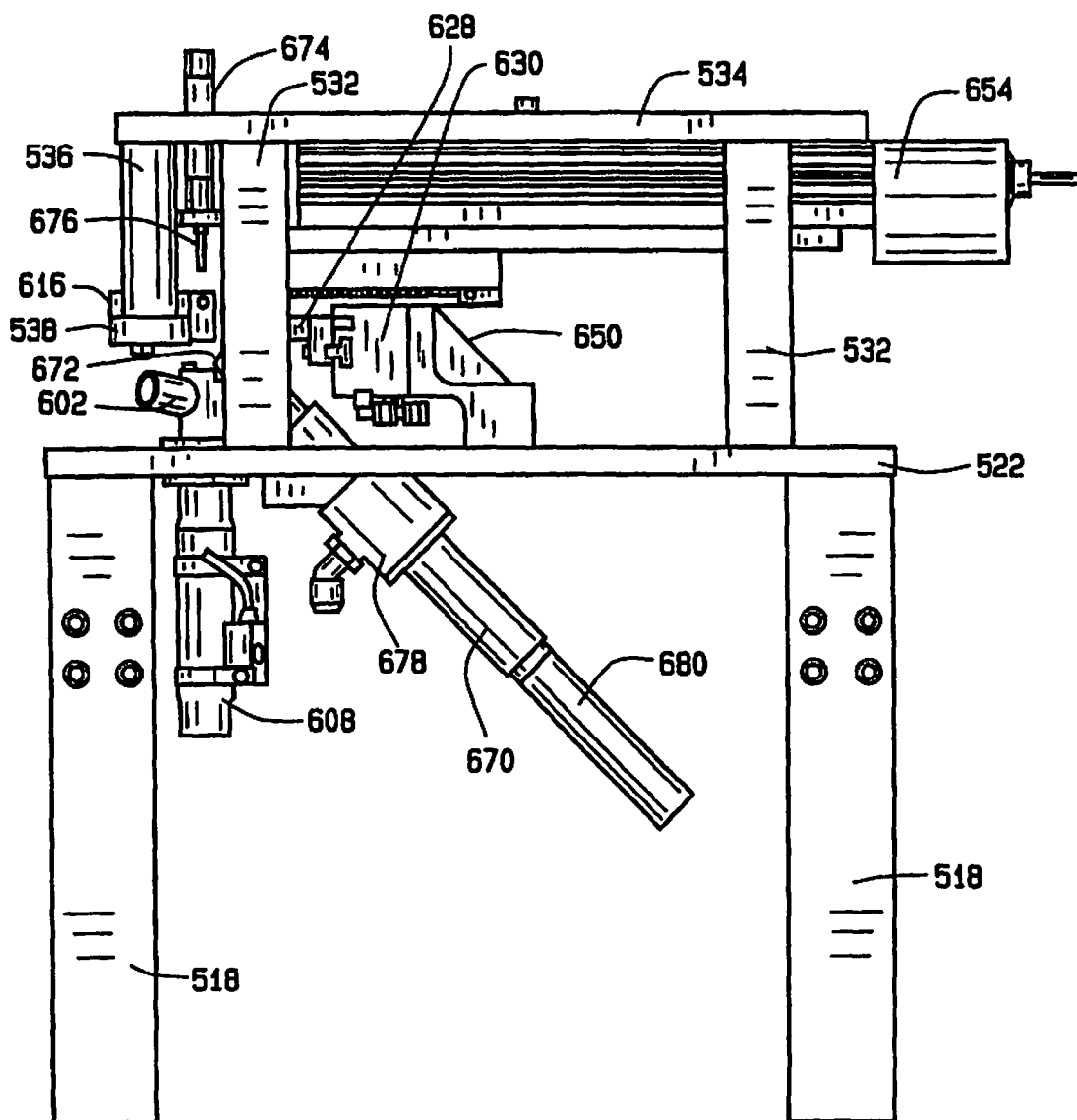
FIG. 19A is a side elevation view of the seed sampling station, with the broach in its retracted position.
Figure 19B:
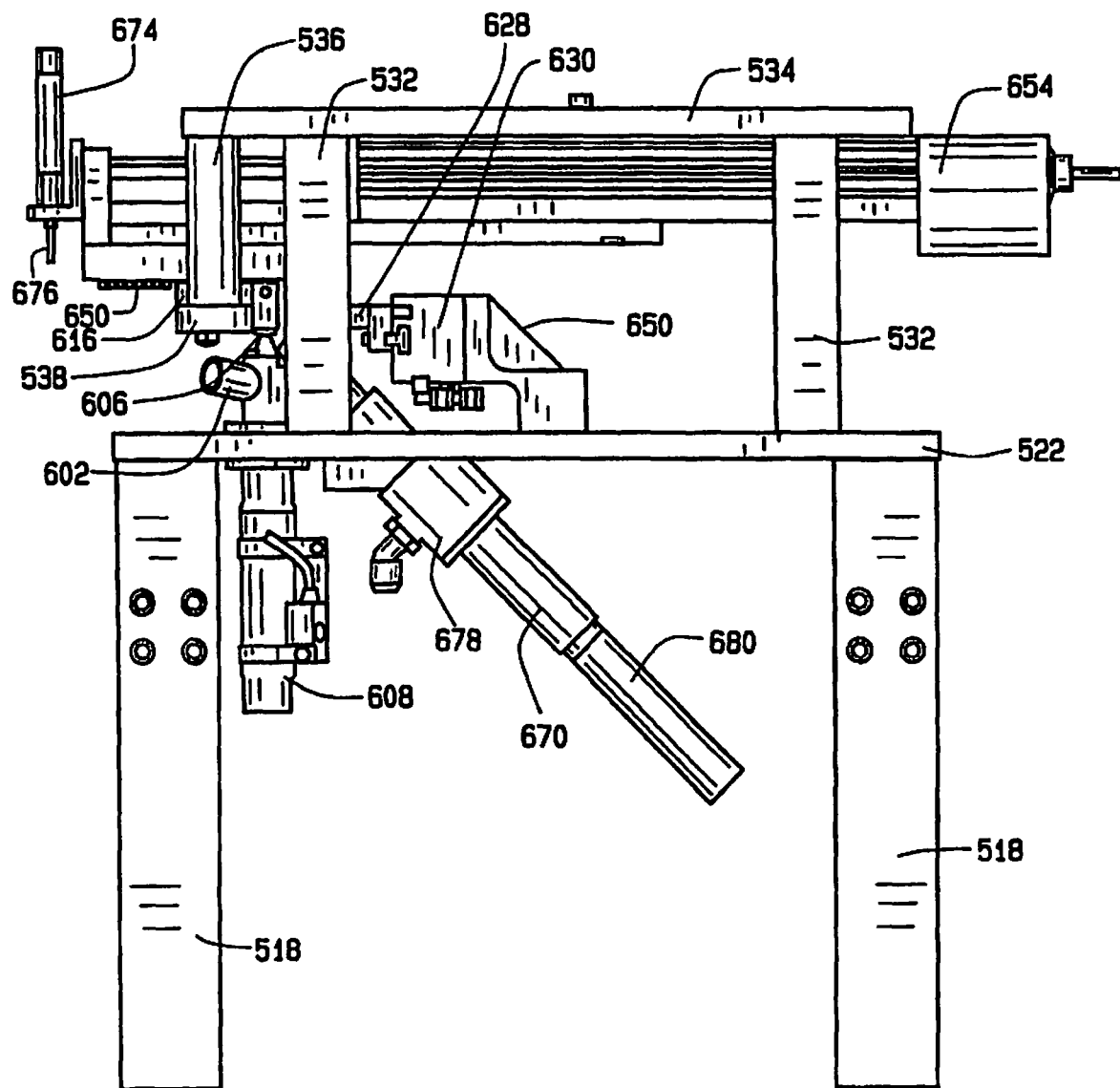
FIG. 19B is a side elevation view of the seed sampling station, with the broach in its extended position.
Figure 20:
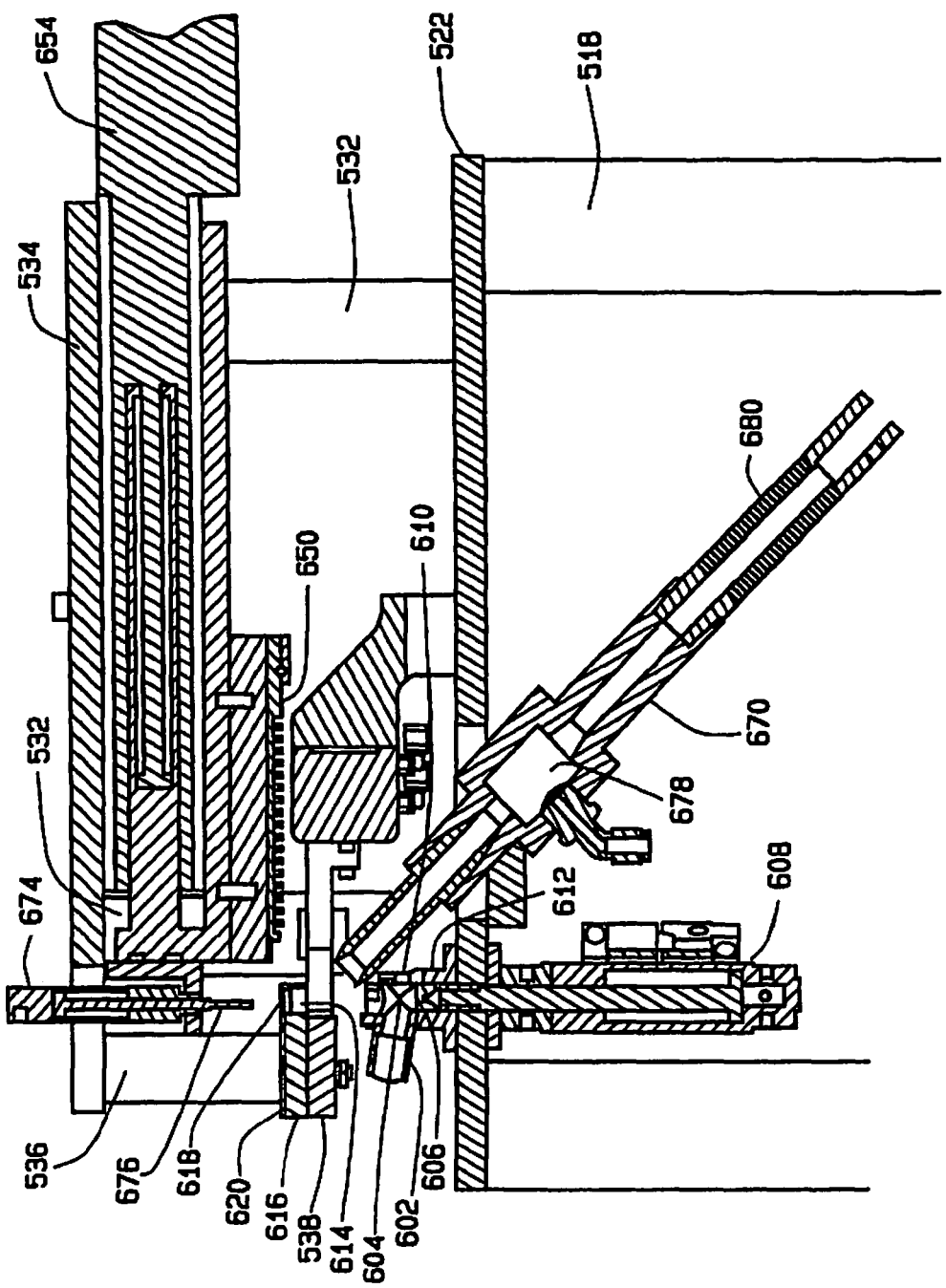
FIG. 20 is a longitudinal cross-sectional view of the seed sampling station.
Figure 21:
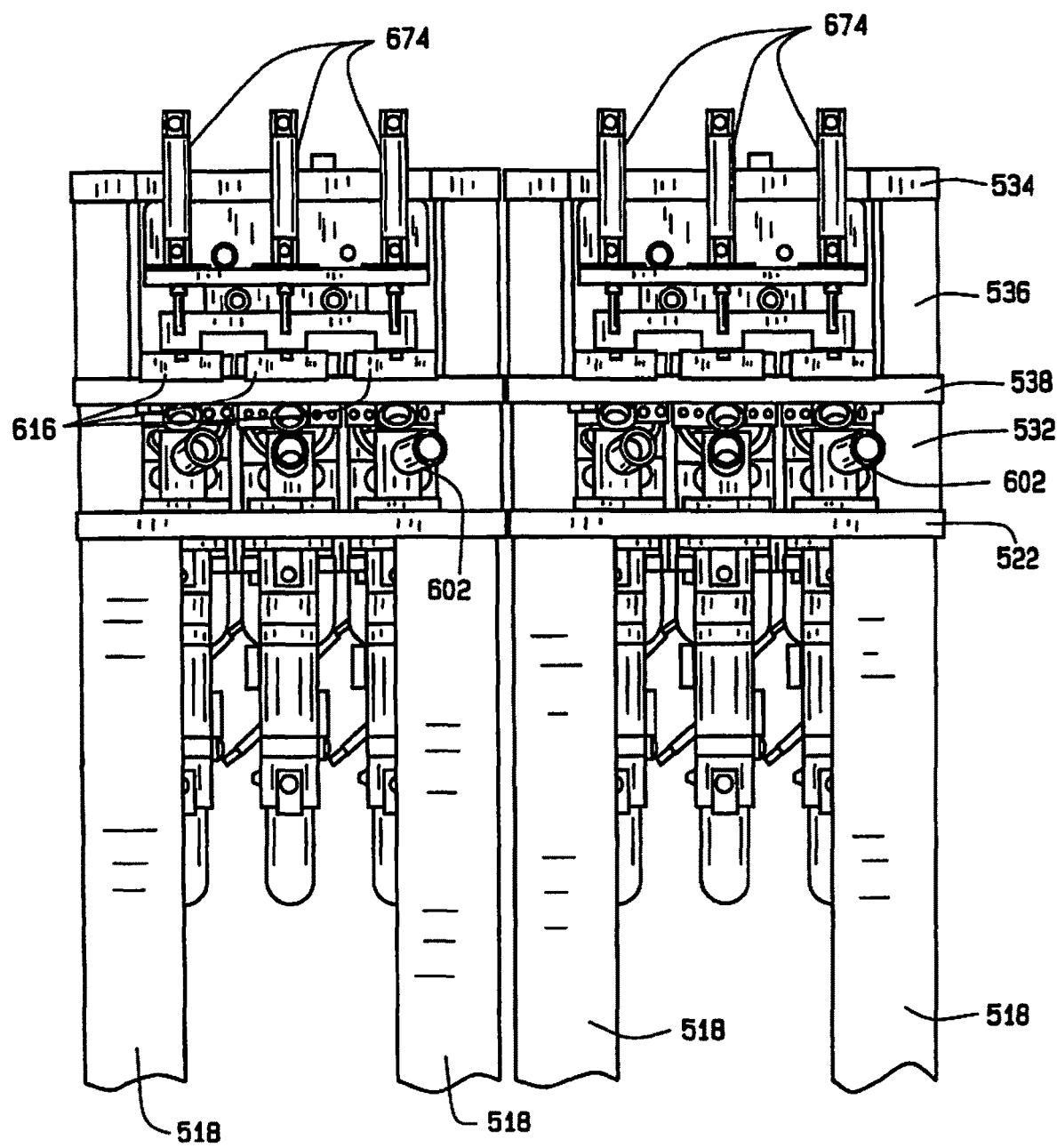
FIG. 21 is a front end elevation view of the seed sampling station.
Figure 22:
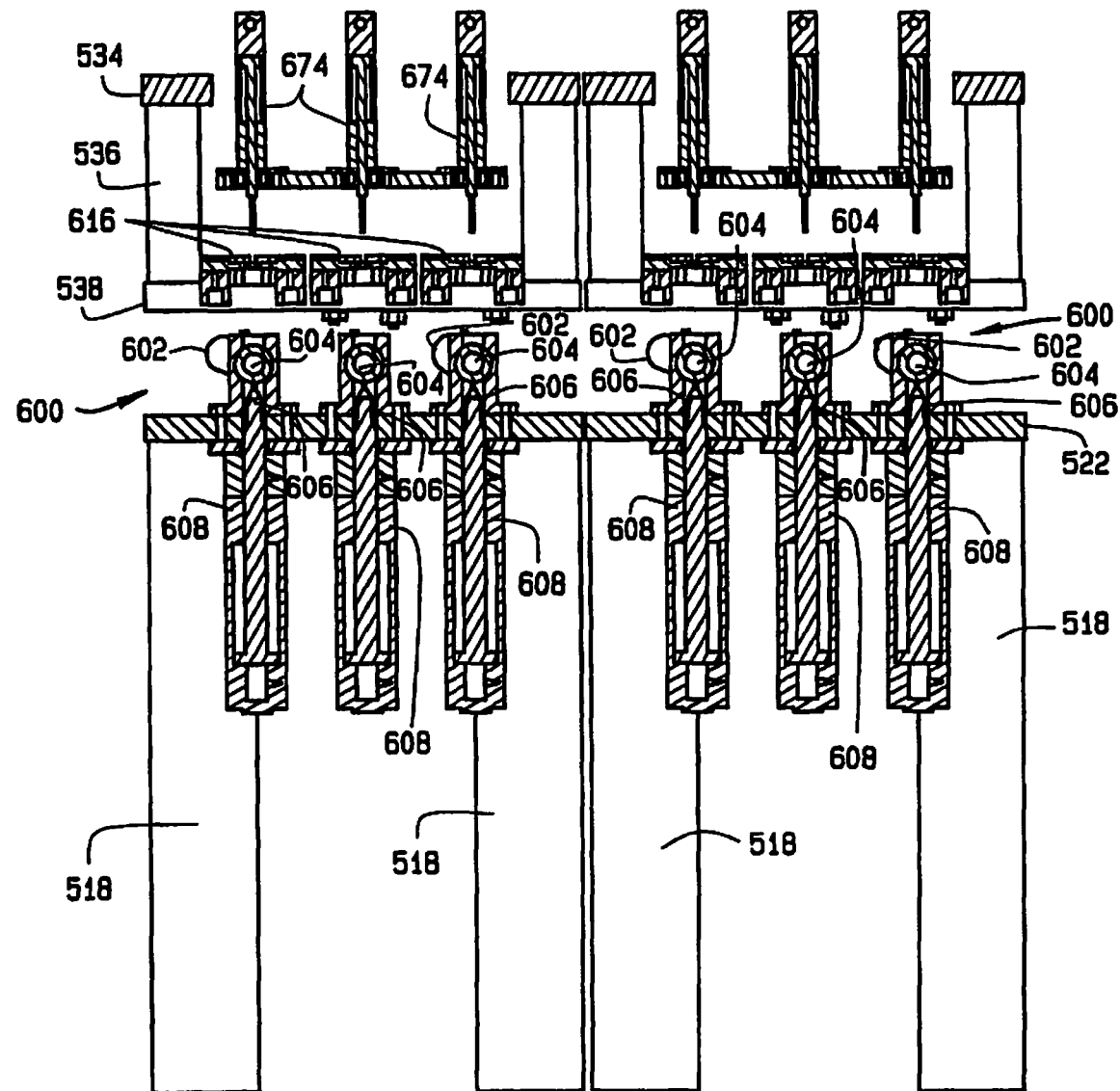
FIG. 22 is a transverse cross-sectional view of the seed sampling station.

The cutting edges 652 are staggered, each cutting progressively deeper than the previous. The amount of sample material and the depth of the cut can be controlled by controlling the advancement of the broach 650. For smaller samples and shallower depths of cut, the stroke of the broach 650 is shorter, and for larger samples or deeper depths of cut, the stroke of the broach is longer. For partial strokes, tissue from the seed may be trapped between edges 652. The broach 650 can be advanced and retracted to help release all of the sample. For example, after the seed is released, the broach may be advanced and retracted to help remove seed tissue trapped between the cutting edges. The full range of travel of the broach 650 is shown in FIGS. 19A and 19B.

The sampling broach 650 is preferably driven by a linear actuator 654. In the preferred embodiment, three broaches 650 are driven by a single actuator 654. Using a single actuator to operate multiple broaches saves space and is more economical.

A sample transport system 656 comprising a conduit 658 having an inlet 660 communicating with a passage 662 that opens to the sampling opening 618 and the groove 620 in the sampling plate 616 removes tissue samples made by the action of the cutting edges 652 of the sampling broach 650. The conduit 658 transports the sample to outlet 664 where it is deposited in a unique sample holder in the sample handling station 504. This sample holder may be, for example, a well 666 in a tray 668 mounted on a x-y indexing table 670 on cart 510, so that the relationship between samples and their respective seeds can be determined. The sample transport system 656 includes an air jet 672 which induces air flow through the conduit 658 to move the sample through the conduit.

A second sampling mechanism can be mounted on the linear actuator 654 and moves with the broach 650. The second sampling mechanism can comprise a coring device 674 having a coring tool 676 for taking a plug sample of the seed from the kerf made by the broach 650. This tissue in this sample is from a deeper location than the tissue scraped by the broach 650, and provides different information. In some embodiments the material removed by the broach 650 might simply be discarded, and only the sample taken with the coring device 674 retained. In some embodiments both samples may be retained and separately stored for separate testing. In still other embodiments the only sample is the sample removed by the broach 650. In embodiments without the second sampling mechanism, the coring device 674 and coring tool 676 can be replaced with an actuator with a simple push rod that extends through the sampling opening 618 to help push a seed in the recess 614.

A seed transport system 680 having an inlet 682 adjacent recess 614 for drawing in seeds after they are released by the fingers 626 and 628 and the rod 606 lowers the seed after the sampling operation. The seed transport system 680 transports the seeds to a unique seed holder in the seed handling station 506 on the cart 512. This seed holder may be, for example, a well 684 in a tray 686 mounted on an x-y indexing table 688 on cart 612, so that the relationship between samples and their respective seeds can be determined. The seed transport mechanism 680 includes an air jet 690 which induces air flow through the conduit 680 to move the sample through the conduit.

Operation

In operation, a plurality of seeds, e.g. soybean seeds, are dumped into the hopper 550 of the sampling system 500. These seeds flow under gravity toward the disk 552, suction through the ports 556 hold one seed in each cavity 554. As the disk 552 is rotated by the indexing motor 560, individual seeds are wiped from the disk by the wiper 562, and fall under gravity through the guide 564 to the outlet. The linear actuator 586 moves the distributor 566 so that each passage 570 of the distributor aligns with the guide 564 to load one seed through the opening 576 and into passage 570. When all of the passages 570 in the distributor 566 are full, the linear actuator 586 moves the distributor into position to load its seeds into sampling stations 600 in the seed chipper 516. The sleeves 572 and 574 are moved by actuator 580, which aligns the openings 578 with the passages 570, allowing the seeds in the passages 570 to fall into the tubes 592 that lead to the sampling units 600. The nozzles 590 provide a blast of air that helps urge the seeds from the passages 570 through the tubes 592 to the chambers 604 in the sampling units 600.

Preferably all of the passages 570 are loaded in series and discharge their seeds simultaneously to the sampling units 600, but the distributor could be programmed to operate in some other manner. Once the seeds arrive in the sampling stations 600, the rods 606 lift the seeds into the recesses 614 in the underside of the plates 616. The recesses 614 may be sized and shaped to help optimally orient the seed. In the recesses 614, a portion of the seeds protrude through the sampling holes 618 and into the grooves 620. The broaches 650 are translated in the grooves 620, allowing their cutting edges 652 to remove material from the portions of the seeds protruding into the grooves 620, and forming small kerfs in the seeds. As each broach 650 removes material, the sample transport system 656 draws the sample material through passage 662 and into the inlet 660. The samples travel in conduits 658 away from the sampling stations 600 to a sample storage location, such as wells 666 in a sample tray 668. A second sample can be taken by the coring tool 676 of sampling device 674 through the opening 618 in the sampling plate 616. After the sampling is completed, the rod 606 retracts, and as the seed drops the sampled-seed transport system 680 transports the sampled seed to a seed storage location, such as a well 684 in a seed tray 686.

The indexing tables 670 and 688 move to align different wells with the outlets of the sample transport system 656 and the seed transport system 680, and the sample process is repeated. When all of the wells 666 in a sample tray 668 are full, the samples in the sample tray can be tested, and the seeds in the corresponding seed tray 686 can be selected based upon the results of the testing of samples. The sampling preferably does not substantially adversely affect the viability of the seeds.

Applications

The present disclosure provides methods for analyzing seeds having a desired trait, marker or genotype. In one aspect of the disclosure, the analytical methods allow individual seeds to be analyzed that are present in a batch or a bulk population of seeds such that the chemical and/or genetic characteristics of the individual seeds can be determined.

Samples prepared by the present disclosure can be used for determining a wide variety of physical, chemical and/or genetic traits. Examples of chemical analyses for use in the methods of the present disclosure include starch content, protein content, oil content, determination of fatty acid profiles, etc.

In one embodiment, the methods and devices of the present disclosure can be used in a breeding program to select plants or seeds having a desired trait or marker genotype. The methods of the present disclosure can be used in combination with any breeding methodology and can be used to select a single generation or to select multiple generations. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches for breeding the plants of the present disclosure are set forth below. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

In a particular embodiment, the methods of the present disclosure are used to determine the genetic characteristics of seeds in a marker-assisted breeding program. Such methods allow for improved marker-assisted breeding programs wherein nondestructive direct seed sampling can be conducted while maintaining the identity of individuals from the seed sampler to the field. As a result, the marker-assisted breeding program results in a "high-throughput" platform wherein a population of seeds having a desired trait, marker or genotype can be more effectively bulked in a shorter period of time, with less field and labor resources required. Such advantages will be more fully described below.

In one embodiment, the present disclosure provides a method for analyzing individual seeds within a population of seeds having genetic differences. The method comprises removing a sample comprising cells with DNA from seeds in the population without affecting the germination viability of the seeds; screening the DNA extracted from the sample for the presence or absence of at least one genetic marker; selecting seeds from the population based upon the results of the DNA screening; and cultivating plants from the selected seed.

As described above, the sampling systems and methods of this disclosure protect germination viability of the seeds so as to be non-destructive. Germination viability means that a predominant number of sampled seeds, (i.e, greater than 50% of all sampled seeds) remain viable after sampling. In a particular embodiment, at least about 75% of sampled seeds, and in some embodiments at least about 85% of sampled seeds remain viable. It should be noted that lower rates of germination viability may be tolerable under certain circumstances or for certain applications, for example, as genotyping costs decrease with time because a greater number of seeds could be sampled for the same genotype cost.

In another embodiment, germination viability is maintained for at least about six months after sampling to ensure that the sampled seed will be viable until it reaches the field for planting. In a particular embodiment, the methods of the present disclosure further comprise treating the sampled seeds to maintain germination viability. Such treatment may generally include any means known in the art for protecting a seed from environmental conditions while in storage or transport. For example, in one embodiment, the sampled seeds may be treated with a polymer and/or a fungicide to protect the sampled seed while in storage or in transport to the field before planting.

DNA may be extracted from the sample using any DNA extraction methods known to those of skill in the art which will provide sufficient DNA yield, DNA quality, and PCR response. A non-limiting example of suitable DNA-extraction methods is SDS-based extraction with centrifugation. In addition, the extracted DNA may be amplified after extraction using any amplification method known to those skilled in the art. For example, one suitable amplification method is the GenomiPhi® DNA amplification prep from Amersham Biosciences.

The extracted DNA is screened for the presence or absence of a suitable genetic marker. A wide variety of genetic markers are available and known to those of skill in the art. The DNA screening for the presence or absence of the genetic marker can be used for the selection of seeds in a breeding population. The screening may be used to select for quantitative trait loci (QTL), alleles, or genomic regions (haplotypes). The alleles, QTL, or haplotypes to be selected for can be identified using newer techniques of molecular biology with modifications of classical breeding strategies.

In one embodiment, the seed is selected based on the presence or absence of a genetic marker that is genetically linked with a QTL. Examples of QTLs which are often of interest include but are not limited to yield, lodging resistance, height, maturity, disease resistance, pest resistance, resistance to nutrient deficiency, and grain composition. Alternatively, the seed can be selected based on the presence or absence of a marker that is genetically linked with a haplotype associated with a QTL. Examples of such QTL may again include without limitation yield, lodging resistance, height, maturity, disease resistance, pest resistance, resistance to nutrient deficiency, and grain composition.

Selection of a breeding population could be initiated as early as the $F_2$ breeding level, if homozygous inbred parents are used in the initial breeding cross. An $F_1$ generation could also be sampled and advanced if one or more of the parents of the cross are heterozygous for the alleles or markers of interest. The breeder may screen an $F_2$ population to retrieve the marker genotype of every individual in the population. Initial population sizes, limited only by the number of available seeds for screening, can be adjusted to meet the desired probability of successfully identifying the desired number of individuals. See Sedcole, J. R. "Number of plants necessary to recover a trait." *Crop Sci.* 17:667-68 (1977). Accordingly, the probability of finding the desired genotype, the initial population size, and the targeted resulting population size can be modified for various breeding methodologies and inbreeding level of the sampled population.

The selected seeds may be bulked or kept separate depending on the breeding methodology and target. For example, when a breeder is screening an $F_2$ population for disease resistance, all individuals with the desired genotype may be bulked and planted in the breeding nursery. Conversely, if multiple QTL with varying effects for a trait such as grain yield are being selected from a given population, the breeder may keep individual identity preserved, going to the field to differentiate individuals with various combinations of the target QTL.

Several methods of preserving single seed identity can be used while transferring seed from the chipping lab to the field. Methods include, but are not limited to, transferring selected individuals to seed tape, a cassette tray, or indexing tray, transplanting with peat pots, and hand-planting from individual seed packets.

Multiple cycles of selection can be utilized depending on breeding targets and genetic complexity.

Advantages of using the screening methods of this disclosure include, without limitation, reduction of labor and field resources required per population or breeding line, increased capacity to evaluate a larger number of breeding populations per field unit, and increased capacity to screen breeding populations for desired traits prior to planting. Field resources per population are reduced by limiting the field space required to advance the desired genotypes. For example, a population of 1,000 individuals may be planted at 25 seeds per row consuming a total of 40 rows in the field. Using conventional tissue sampling, all 1,000 plants would be tagged and manually sampled by scoring leaf tissue. Molecular marker results would be needed prior to pollination and only those plants containing the desired genetic composition would be pollinated. Thus, if it was determined that 50 seeds contained the desired genetic composition, conventional breeding methodology would have required the planting of 1000 plants to obtain 50 seeds. By contrast, the screening methods of this disclosure allow the breeder to screen the 1,000 seeds in the lab and select the 50 desired seeds prior to planting. The 50 individuals can then be planted in the field, consuming only two 25 seed rows. Additionally, the screening methods of this disclosure do not require tagging or sampling in the field, thereby significantly reducing the required manual labor resources.

In addition to reducing the number of field rows per population, the screening methods of this disclosure may further increase the number of populations the breeder can evaluate in a given breeding nursery. Using the above example wherein 50 seeds out of each population of 1000 seeds contained the desired genetic composition, a breeder applying the methods of this disclosure could evaluate 20 populations of 50 seeds each using the same field area consumed by a single population using conventional field tissue sampling techniques. Even if the populations are selected for a single allele, using a 1:2:1 expected segregation ratio for an $F_2$ population, the breeder could evaluate 4 populations in the same field area as a single field tissue sampled population.

A potential further advantage to seed chipping is that it could be used to mitigate the risks associated with growing plants in certain geographies where plants may grow poorly or experience poor environmental conditions, or may even be destroyed during storms. For example, seeds with the "best" genotype or marker composition could be planted in geography 1 and seeds with the "next best" genotype could be planted in geography 2. In this case geography 2 would be a backup in case any problem befell the plants grown in geography 1. This is very difficult to do with the traditional method of taking tissue samples from germinated plants for genotyping, because these plants would then need to be uprooted and transplanted to the second geography. Using the methods of this disclosure avoids the problem of transplantation.

The screening methods of the disclosure may further be used in a breeding program for introgressing a trait into a plant. Such methods comprise removing a sample comprising cells with DNA from seeds in a population, screening the DNA extracted from each seed for the presence or absence of at least one genetic marker, selecting seeds from the population based upon the results of the DNA screening; cultivating a fertile plant from the seed; and utilizing the fertile plant as either a female parent or male parent in a cross with another plant.

Examples of genetic screening to select seeds for trait integration include, without limitation, identification of high recurrent parent allele frequencies, tracking of transgenes of interest or screening for the absence of unwanted transgenes, selection of hybrid testing seed, and zygosity testing.

The identification of high recurrent pair allele frequencies via the screening methods of the present disclosure again allows for a reduced number of rows per population and an increased number of populations, or inbred lines, to be planted in a given field unit. Thus, the screening methods of the present disclosure may also effectively reduce the resources required to complete the conversion of inbred lines.

The methods of the present disclosure further provide quality assurance (QA) and quality control by assuring that regulated or unwanted transgenes are identified and discarded prior to planting. This application in a QA capacity could effectively eliminate unintentional release infractions.

The methods of the present disclosure may be further applied to identify hybrid seed for transgene testing. For example, in a conversion of an inbred line at the BCnFi stage, a breeder could effectively create a hybrid seed lot (barring gamete selection) that was 50% hemizygous for the trait of interest and 50% homozygous for the lack of the trait in order to generate hybrid seed for testing. The breeder could then screen all $F_1$ seeds produced in the test cross and identify and select those seeds that were hemizygous. Such method is advantageous in that inferences from the hybrid trials would represent commercial hybrid genetics with regard to trait zygosity.

Other applications of the screening methods of this disclosure for identifying and tracking traits of interest carry the same advantages identified above with respect to required field and labor resources. Generally, transgenic conversion programs are executed in multi-season locations which carry a much higher land and management cost structure. As such, the impact of either reducing the row needs per population or increasing the number of populations within a given field unit are significantly more dramatic on a cost basis versus temperate applications.

Still further, the screening methods of this disclosure may be used to improve the efficiency of the doubled haploid program through selection of desired genotypes at the haploid stage and identification of ploidy level to eliminate non-haploid seeds from being processed and advancing to the field. Both applications again result in the reduction of field resources per population and the capability to evaluate a larger number of populations within a given field unit.

In another embodiment, the disclosure further provides an assay for predicting embryo zygosity for a particular gene of interest (GOI). The assay predicts embryo zygosity based on the ratio of the relative copy numbers of a GOI and of an internal control (IC) gene per cell or per genome. Generally, this assay uses an IC gene that is of known zygosity, e.g., homozygous at the locus (two IC copies per diploid cell), for normalizing measurement of the GOI. The ratio of the relative copy numbers of the IC to the GOI predicts the GOI copy number in the cell. In a homozygous cell, for any given gene (or unique genetic sequence), the gene copy number is equal to the cell's ploidy level since the sequence is present at the same locus in all homologous chromosomes. When a cell is heterozygous for a particular gene, the gene copy number will be lower than the cell's ploidy level. The zygosity of a cell at any locus can thus be determined by the gene copy number in the cell.

In a particular embodiment, the disclosure provides an assay for predicting corn embryo zygosity. In corn seed, the endosperm tissue is triploid, whereas the embryo tissue is diploid. Endosperm that is homozygous for the IC will contain three IC copies. Endosperm GOI copy number can range from 0 (homozygous negative) to 3 (homozygous positive); and endosperm GOI copy number of 1 or 2 is found in seed heterozygous for the GOI (or hemizygous for the GOI if the GOI is a transgene). Endosperm copy number is reflective of the zygosity of the embryo: a homozygous (positive or negative) endosperm accompanies a homozygous embryo, heterozygous endosperm (whether a GOI copy number of 1 or 2) reflects a heterozygous (GOI copy number of 1) embryo. The endosperm GOI copy number (which can range from 0 to 3 copies) can be determined from the ratio of endosperm IC copy number to endosperm GOI copy number (which can range from 0/3 to 3/3, that is, from 0 to 1), which can then be used to predict zygosity of the embryo.

Copy numbers of the GOI or of the IC can be determined by any convenient assay technique for quantification of copy numbers, as is known in the art. Examples of suitable assays include, but are not limited to, Real Time (TaqMan®) PCR (Applied Biosystems, Foster City, Calif.) and Invader® (Third Wave Technologies, Madison, Wis.) assays. Preferably, such assays are developed in such a way that the amplification efficiency of both the IC and GOI sequences are equal or very similar. For example, in a Real Time TaqMan® PCR assay, the signal from a single-copy GOI (the source cell is determined to be heterozygous for the GOI) will be detected one amplification cycle later than the signal from a two-copy IC, because the amount of the GOI is half that of the IC. For the same heterozygous sample, an Invader® assay would measure a GOI/IC ratio of about 1:2 or 0.5. For a sample that is homozygous for both the GOI and the IC, the GOI signal would be detected at the same time as the IC signal (TaqMan®), and the Invader assay would measure a GOI/IC ratio of about 2:2 or 1.

These guidelines apply to any polyploid cell, or to haploid cells (such as pollen cells), since the copy number of the GOI or of the IC remain proportional to the genome copy number (or ploidy level) of the cell. Thus, these zygosity assays can be performed on triploid tissues such as corn endosperm.

EXAMPLES

The following examples are merely illustrative, and not limiting to this disclosure in any way.

Example 1

This example describes an assay for predicting the zygosity of corn embryos using an internal control (IC) gene homozygous at the locus (i.e., two IC copies in the diploid embryo and three IC copies in the triploid endosperm). In an inbred line of a diploid (or higher ploidy) organism such as corn, the endogenous internal control is typically homozygous; transgenic events in such organisms at the first generation (termed "RO" in corn) are typically hemizygous (that is, the transgene is typically present in only one of the two or more homologous chromosomes). Corn (Zea mays) is a diploid organism, thus a "single copy" RO event has one copy of the GOI per cell, but 0.5 copies per haploid genome, a "two copy" RO event has two copies of the GOI per cell, but 1 copy per haploid genome, and so forth.

In this example, tubulin was used as the IC gene, and the GOI was a transgene encoding neomycin phosphotransferase II (NPT II), which is used for kanamycin resistance selection. Endosperm (triploid) tissue was taken from seed (either by hand sampling or by scraping a seed with an automated sampler of the present disclosure). The endosperm-sampled seed was germinated, and leaf tissue (diploid) from successfully germinated plants was also sampled for genetic analysis. The leaf tissue correlates directly with embryo zygosity and was thus used to demonstrate that endosperm zygosity generally predicted zygosity of the embryo and to confirm homozygosity calls from the endosperm. Total genomic DNA was extracted from endosperm tissue and from leaf tissue, and quantitatively analyzed using an Invader® assay with oligonucleotide probes specific for the gene of interest, NPT II, or for the internal control gene, tubulin. The ratio of the GOI to IC was measured using conventional molecular biology techniques. See Table 1. A summary of results of multiple experiments are shown in Table 2.

Results indicated that endosperm zygosity generally predicted zygosity of the embryo (as indicated by the leaf zygosity) and was reliable in predicting homozygosity for all seeds that germinated. Furthermore, endosperm zygosity analysis gave few false-negative homozygous predictions (especially when the endosperm tissue was obtained with the automated sampler). These results demonstrate that for a cell of a known ploidy level, the ratio of copy number of a GOI to that of an IC indicates the zygosity of that cell. Furthermore, the zygosity assay of the present disclosure can predict zygosity of one tissue based on the zygosity of another, that is, the assay can predict the embryo zygosity based on the endosperm zygosity.

TABLE 1

| Automated Ratio | Automated Zygosity | Manual Ratio | Manual Zygosity |
|---|---|---|---|
| 1.39 | Heterozygous | 1.42 | Heterozygous |
| 0.14 | neg homozygous | 0.12 | neg homozygous |
| 0.08 | neg homozygous | 0.08 | neg homozygous |
| 0.13 | neg homozygous | 0.10 | neg homozygous |
| 0.10 | neg homozygous | 0.08 | neg homozygous |
| 1.55 | Heterozygous | 1.38 | Heterozygous |
| 0.84 | Heterozygous | 1.45 | Heterozygous |
| 0.14 | neg homozygous | 1.48 | Heterozygous |
| 1.48 | Heterozygous | 1.37 | Heterozygous |
| 1.39 | Heterozygous | 1.47 | Heterozygous |
| 2.03 | POS homozygous | 1.93 | POS homozygous |
| 0.13 | neg homozygous | 0.05 | neg homozygous |
| 1.71 | inconclusive | 1.81 | POS homozygous |
| 0.81 | Heterozygous | 1.41 | Heterozygous |
| 1.84 | POS homozygous | 1.77 | POS homozygous |
| 1.54 | Heterozygous | 1.43 | Heterozygous |
| 1.48 | Heterozygous | 1.50 | Heterozygous |
| 0.92 | Heterozygous | 1.40 | Heterozygous |
| 1.51 | Heterozygous | 1.42 | Heterozygous |
| 1.60 | Heterozygous | 1.37 | Heterozygous |
| 0.86 | Heterozygous | 1.47 | Heterozygous |
| 1.81 | POS homozygous | 2.02 | POS homozygous |
| 0.15 | neg homozygous | Low DNA | |
| 1.89 | POS homozygous | 1.85 | POS homozygous |
| 0.21 | neg homozygous | 0.10 | neg homozygous |
| 0.09 | neg homozygous | 0.11 | neg homozygous |
| 0.89 | Heterozygous | 1.50 | Heterozygous |
| 1.50 | Heterozygous | 1.37 | Heterozygous |

TABLE 1-continued

| Automated Ratio | Automated Zygosity | Manual Ratio | Manual Zygosity |
|---|---|---|---|
| 1.82 | inconclusive | 2.02 | POS homozygous |
| 2.14 | POS homozygous | 0.99 | inconclusive |
| 1.22 | Heterozygous | 1.44 | Heterozygous |
| 2.22 | POS homozygous | 2.24 | POS homozygous |
| 0.79 | Heterozygous | 1.40 | Heterozygous |
| 1.23 | Heterozygous | 1.47 | Heterozygous |
| 1.49 | Heterozygous | 1.38 | Heterozygous |
| 1.33 | Heterozygous | 1.37 | Heterozygous |

TABLE 2

| Endosperm sampling method | Number of homozygous seeds identified by endosperm analysis | Number of predicted homozygous seeds that did not germinate | Number of confirmed homozygous calls based on leaf analysis | Number of false negative homozygous calls based on endosperm analysis |
|---|---|---|---|---|
| Hand | 8 out of 36 | 0 | 8 (all) | 5 (13.9%) |
| Automated | 6 out of 24 | 1 | 5 | 0 |
| Hand | 6 out of 36 | 0 | 6 (all) | 2 (5.6%) |
| Automated | 6 out of 24 | 1 | 5 | 0 |
| Hand | 5 out of 36 | 0 | 5 (all) | 7 (19.4%) |
| Automated | 7 out of 24 | 2 | 5 | 0 |
| Hand | 7 out of 36 | 1 | 6 | 0 |
| Automated | 5 out of 24 | 2 | 3 | 0 |

Example 2

This example demonstrates the use of the screening methods of the present disclosure in a program for marker-assisted selection of soybeans for Low Linoleic Acid.

Soybean is the most valuable legume crop, with many nutritional and industrial uses due to its unique chemical composition. Soybean seeds are an important source of vegetable oil, which is used in food products throughout the world. The relatively high level (usually about 8%) of linolenic acid (18:3) in soybean oil reduces its stability and flavor. Hydrogenation of soybean oil is used to lower the level of linolenic acid (18:3) and improve both stability and flavor of soybean oils. However, hydrogenation results in the production of trans fatty acids, which increases the risk for coronary heart disease when consumed. The development of low linolenic acid soybean has been complicated by the quantitative nature of the trait. The low linolenic acid soybean varieties that have been developed have been found to yield poorly, limiting their usefulness in most commercial settings. Developing a product with commercially significance seed yield is a high priority in most soybean cultivar development programs.

An example of the application of the screening methods of the present disclosure is selection of soybean plants with both high yield and decreased linoleic acid content Soybean progeny performance as it relates to low linoleic acid relies mainly on two major quantitative trait locus (QTL) at Fad3-1b and Fad3-1c. Analysis of segregating plants demonstrated that Fad3-1b and Fad3-1c additively control linolenic content in soybean. Therefore, by using a combination of markers for Fad3-1b and Fad3-1c, a breeder using the disclosure can accurately predict linolenic acid content in soybean plants. The markers can be used to infer the genotypic state of a seed at any stage in the breeding process, for example, at the finished inbred line stage, or the $F_1$, $F_2$, $F_3$, etc.

A seminal $F_1$ hybrid can be produced by crossing two inbred soybean lines (for example, crossing a plant containing the Fad3-1b and/or Fad3-1c alleles associated with decreased linoleic acid content to a plant lacking these alleles) followed by natural self-pollination. Since the markers can be used to infer the genotypic state of a single seed obtained from an intermating of such inbred lines, early generation (i.e., $F_2$) marker-assisted breeding can be conducted.

Soybean seed at ambient temperature and humidity typically equilibrate to 8% moisture on a dry weight basis. Soybean seed at this level of moisture tends to split when chipped. To reduce splitting, seed should be humidified to moisture level of 12%. When pretreated in this manner, splitting is significantly reduced to <5%.

The selected $F_2$ seed that have the desired genotype may be bulked or kept separate depending on the breeding objectives. If multiple QTL with varying effects were being selected from a given population, the breeder could preserve single seed identity to differentiate individuals with various combinations of the target resistance QTL. These seeds could be planted in the field with appropriate field identification. Several methods of preserving single seed identity can be used while transferring seed from the chipping lab to the field. Methods include transferring selected individuals to horticultural seed tape that could also include radio frequency identification to aid in the identification of the individual genotyped seed. Other methods would be to use an indexing tray, plant seeds in peat pots and then transplant them, or hand plant from individual seed packets.

Example 3

This example demonstrates the use of the screening methods of the present disclosure in a program for recurrent parent alleles in a backcross breeding program.

The screening methods of the present disclosure can be used for selection of transgenes as well as identification of recurrent parent alleles. The identification of genotypes with desired recurrent parent allele frequencies before planting allows the number of rows per population to be reduced throughout the entire breeding program along with an increase in the number of populations included in the conversion program within a given field unit. This results in improved land usage, reduced land and labor costs, etc.

Figure 29:
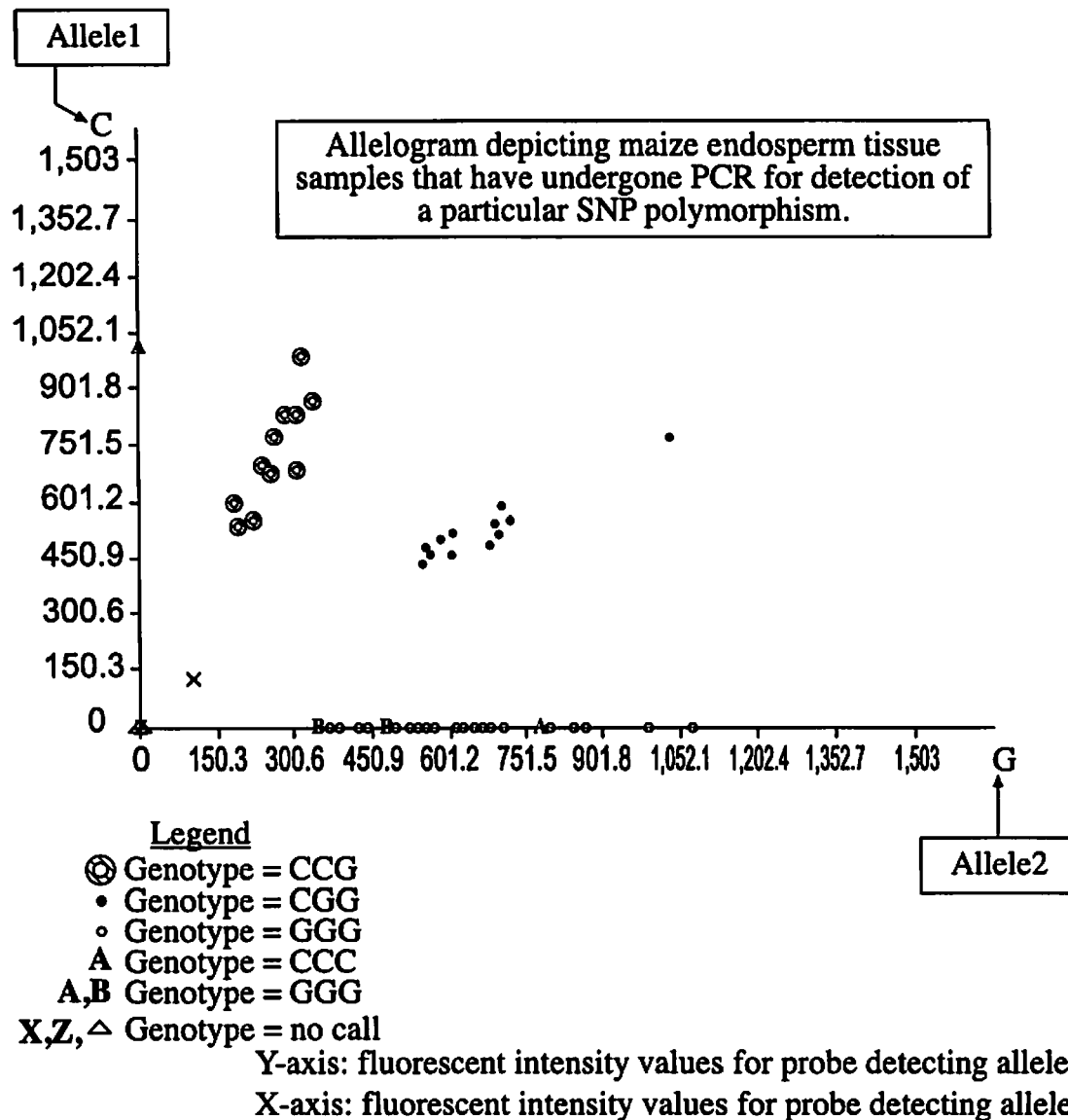
FIG. 29 is an Allelogram depicting maize endosperm tissue samples that have undergone PCR for detection of a particular SNP polymorphism.

An example of screening endosperm tissue from corn for recurrent parent alleles in a backcross breeding program is shown in FIG. 29.

Example 4

This example demonstrates the use of the screening methods of the present disclosure for use in DNA line fingerprinting and linkage phase determination.

Combined with bulking of a single seed's DNA, line fingerprinting could be accomplished without the need to sample the line in the field.

By using seed endosperm tissue (seed coat in soybean) derived from a diploid plant, the parental marker haplotypes can be determined using a genotyping system that enables detection of different allele frequencies in DNA samples. Since endosperm tissue is triploid, with two copies derived from the female gamete, the linkage phase of the parental line can be derived by dissecting heterozygous progeny genotypes. The DNA sample from endosperm tissue allows for a determination of the ploidy level of the genetic marker. A diploid ploidy level in the genetic marker indicates maternal inheritance and a haploid ploidy level in the genetic marker indicates paternal inheritance.

What is claimed is:

1. An automated method for sampling seeds, the automated method comprising:
    removing material from a seed at an automated sampling station; and
    after removing the material from the seed, detecting, by at least one sensor, movement of the seed out of the automated sampling station.

2. The automated method of claim 1, further comprising, after removing the material from the seed, transferring the seed from the automated sampling station to a seed container.

3. The automated method of claim 2, further comprising transferring the material removed from the seed from the automated sampling station to a sample container.

4. The automated method of claim 2, further comprising detecting, by the at least one sensor, the transfer of the seed to the seed container.

5. The automated method of claim 4, wherein the at least one sensor includes a first sensor and a second sensor;
    wherein detecting the movement of the seed out of the automated sampling station includes detecting, by the first sensor, receipt of the seed from the automated sampling station by a conveyor; and
    wherein detecting the transfer of the seed from the automated sampling station to the seed container includes detecting, by the second sensor, removal of the seed from the conveyor to the seed container.

6. The automated method of claim 5, wherein the conveyor includes a tube disposed generally between the automated sampling station and the seed container; and
    wherein transferring the seed from the automated sampling station to the seed container includes inducing an air flow in the tube to thereby draw the seed into the tube from the automated sampling station and move the seed through the tube to the seed container.

7. The automated method of claim 6, further comprising adjusting the air flow in the tube based on the detected receipt of the seed in the tube by the first sensor and/or the detected removal of the seed from the tube by the second sensor.

8. The automated method of claim 5, wherein the first sensor and/or the second sensor includes an optical sensor.

9. The automated method of claim 5, wherein the seed container includes a tray comprising multiple wells; and
    wherein the method further comprises directing, by the conveyor, the seed to one of the multiple wells of the tray.

10. The automated method of claim 2, wherein detecting the movement of the seed out of the automated sampling station includes detecting, by the at least one sensor, the transfer of the seed from the automated sampling station to the seed container.

11. The automated method of claim 1, further comprising transferring the material removed from the seed to a sample container.

12. The automated method of claim 11, wherein the sample container includes a tray comprising multiple wells; and
    wherein transferring the material removed from the seed to the sample container includes directing, by a sample conveyor, the material removed from the seed to one of the multiple wells of the tray.

13. The automated method of claim 11, wherein removing material from the seed at the automated sampling station includes removing the material from the seed while protecting germination viability of the seed.

14. The automated method of claim 13, further comprising analyzing the material removed from the seed for one or more characteristics, and then selecting the seed based on presence or absence of the one or more characteristics in the material.

15. The automated method of claim 14, wherein the seed is a corn seed.

16. The automated method of claim 14, wherein the seed is a soybean seed.

* * * * *